(12) United States Patent
Lanos et al.

(10) Patent No.: US 9,494,576 B2
(45) Date of Patent: *Nov. 15, 2016

(54) METHODS FOR DETECTING CONTAMINANTS IN SOLUTIONS CONTAINING GLUCOSE POLYMERS

(75) Inventors: Pierre Lanos, La Bassee (FR); Hela Hacine-Gherbi, Villeneuve D'Ascq (FR); Fabrice Allain, Lille (FR); Mathieu Carpentier, Saint Andre Lez Lille (FR); Agnes Denys, Lille (FR)

(73) Assignee: ROQUETTE FRERES, Lestrem (FR)

( * ) Notice: Subject to any disclaimer, the term of this patent is extended or adjusted under 35 U.S.C. 154(b) by 54 days.

This patent is subject to a terminal disclaimer.

(21) Appl. No.: 14/110,569

(22) PCT Filed: Apr. 6, 2012

(86) PCT No.: PCT/FR2012/050755
§ 371 (c)(1),
(2), (4) Date: Oct. 8, 2013

(87) PCT Pub. No.: WO2012/143647
PCT Pub. Date: Oct. 26, 2012

(65) Prior Publication Data
US 2014/0051097 A1   Feb. 20, 2014

(30) Foreign Application Priority Data

Apr. 8, 2011 (FR) .................................. 11 53050
May 19, 2011 (FR) .................................. 11 54342
Aug. 2, 2011 (FR) .................................. 11 57073
Nov. 29, 2011 (FR) .................................. 11 60921

(51) Int. Cl.
*G01N 33/50* (2006.01)
*C12Q 1/02* (2006.01)
*C12Q 1/22* (2006.01)

(52) U.S. Cl.
CPC ............. *G01N 33/5047* (2013.01); *C12Q 1/02* (2013.01); *C12Q 1/22* (2013.01); *G01N 33/5055* (2013.01)

(58) Field of Classification Search
None
See application file for complete search history.

(56) References Cited

U.S. PATENT DOCUMENTS

2007/0184496 A1   8/2007  Poole et al.
2009/0239819 A1   9/2009  Wang et al.

OTHER PUBLICATIONS

Toll-Like Receptor Signaling. Accessed from http://www.cellsignal.com/contents/science-pathway-research-immunology-and-inflammation/toll-like-receptors-(tlrs)-pathway/pathways-tlr on Feb. 21, 2015.*
Signaling Pathways Activating p38 MAP Kinase. Accessed from http://www.cellsignal.com/common/content/content.jsp?id=pathways-mapk-p38 on Feb. 21, 2015.*
Vowels, B. et al. "Induction of Proinflammatory Cytokines by a Soluble Factor of *Propionibacterium acnes*: Implications for Chronic Inflammatory Acne" *Infection and Immunity*, Aug. 1995, pp. 3158-3165, vol. 63, No. 8.
Glorieux, G. et al. "A novel bio-assay increases the detection yield of microbiological impurity of dialysis fluid, in comparison to the LAL-test" *Nephrol Dial Transplant*, Feb. 2009, pp. 548-554, vol. 24, No. 2.
Written Opinion in International Application No. PCT/FR2012/050755, Jul. 9, 2012, pp. 1-5.
Natsuka, M. et al. "A polymer-type water-soluble peptidoglycan exhibited both Toll-like receptor 2- and NOD2- agonistic activities, resulting in synergistic activation of human monocytic cells" *Innate Immunity*, 2008, pp. 298-308, vol. 14, No. 5.

* cited by examiner

*Primary Examiner* — Brian J Gangle
*Assistant Examiner* — Andrea McCollum
(74) *Attorney, Agent, or Firm* — Saliwanchik, Lloyd & Eisenschenk

(57) ABSTRACT

The invention relates to a method for detecting contaminants of glucose polymers, said contaminants being capable of acting in synergy with one another so as to trigger an inflammatory reaction, characterized in that it comprises an in vitro inflammatory response test using modified cell lines.

16 Claims, 5 Drawing Sheets

METHODS FOR DETECTING CONTAMINANTS IN SOLUTIONS CONTAINING GLUCOSE POLYMERS

CROSS-REFERENCE TO RELATED APPLICATION

This application is the U.S. national stage application of International Patent Application No. PCT/FR2012/050755, filed Apr. 6, 2012.

The present invention relates to methods for detecting contaminants of glucose polymers, in particular circuits for producing glucose polymers, more particularly those for peritoneal dialysis.

By extension, this method also allows the detection of contaminants of glucose polymers, in particular circuits for producing glucose polymers, for enteral and parenteral feeding, or even the feeding of newborn babies.

A subject of the invention is also the need for identifying the pro-inflammatory contaminants.

TECHNICAL BACKGROUND OF THE INVENTION

The Applicant company has chosen to develop its invention in a field which is known for the dangerousness of the contaminants that may be introduced via glucose polymers, said contaminants being responsible for inflammatory reactions that are very harmful to human health: the field of peritoneal dialysis.

Peritoneal dialysis is a type of dialysis of which the objective is to remove waste such as urea, creatinine, excess potassium or surplus water that the kidneys do not manage or no longer manage to purify out of the blood plasma. This medical treatment is indicated in the event of end-stage chronic renal failure.

It is an intracorporeal purification which uses the peritoneum as a dialysis membrane. Toxic waste from the blood crosses the semi-permeable membrane of the peritoneum, to a solution known as a dialysate. The dialysate is introduced into the peritoneal cavity via a permanent catheter. There are two types of peritoneal dialysis:
- CAPD (continuous ambulatory peritoneal dialysis), a treatment which is based on passing through four bags of dialysate per day according to medical prescription,
- APD (automated peritoneal dialysis), a continuous nocturnal treatment which corresponds to approximately 15 liters of dialysate per 8 hours according to medical prescription.

The dialysates most commonly used are composed of a buffer solution (of lactate or of bicarbonate) at acid pH (5.2-5.5) or physiological pH (7.4), to which electrolytes (sodium, calcium, magnesium, chlorine) and an osmotic acid (glucose or a glucose polymer, such as "icodextrin" present in the Extraneal® ambulatory peritoneal dialysis solution sold by the company Baxter) are added.

The glucose polymer, such as icodextrin mentioned above, is preferred to glucose as osmotic agent because, owing to its small size, the glucose which rapidly crosses the peritoneum leads to a loss of osmotic gradient in the 2 to 4 hours of infusion.

The standard glucose polymers are produced by acid or enzymatic hydrolysis of starch from cereals or from tuberous plants.

Acid hydrolysis of starch, which is completely random, or enzymatic hydrolysis thereof, which is slightly more ordered, provides mixtures of glucose (monomer) and glucose chains which comprise very short molecules (oligomers), with a low degree of polymerization (or DP), and very long molecules (polymers), with a high DP. Glucose polymers have, moreover, an extremely varied molecular weight.

In the more particular field of the use of glucose polymers for continuous ambulatory peritoneal dialysis, it very quickly became apparent that these starch hydrolysates (mixture of glucose, and of glucose oligomers and polymers) could not be used as such.

European patent application EP 207 676 teaches that glucose polymers forming clear and colorless solutions at 10% in water, having a weight-average molecular weight (Mw) of 5 000 to 100 000 daltons and a number-average molecular weight (Mn) of less than 8 000 daltons are preferred.

Such glucose polymers also preferably comprise at least 80% of glucose polymers of which the molecular weight is between 5 000 and 50 000 daltons, little or no glucose or glucose polymers with a DP less than or equal to 3 (molecular weight 504) and little or no glucose polymers with a molecular weight greater than 100 000 (DP of about 600).

In other words, the preferred glucose polymers are glucose polymers with a low polydispersity index (value obtained by calculating the Mw/Mn ratio).

The methods proposed in that patent application EP 207 676 for obtaining these glucose polymers with a low polydispersity index from starch hydrolysates consist:
- either in carrying out a fractional precipitation of a maltodextrin with a water-miscible solvent,
- or in carrying out a molecular filtration of this same maltodextrin through various membranes possessing an appropriate cut-off or exclusion threshold.

In the two cases, these methods are aimed at removing at the same time the very high-molecular-weight polymers and the low-molecular-weight monomers or oligomers.

However, these methods do not provide satisfaction both from the point of view of their implementation and from the point of view of the yields and the quality of the products that they make it possible to obtain.

In the interests of developing a method for producing a completely water-soluble glucose polymer with a low polydispersity index preferentially less than 2.5, preferably having an Mn of less than 8 000 daltons and having an Mw of between 12 000 and 20 000 daltons, said method lacking the drawbacks of the prior art, the Applicant company endeavored to solve this problem in its patent EP 667 356, by starting from a hydrolyzed starch rather than from a maltodextrin.

The glucose polymer obtained by chromatographic fractionation then preferably contains less than 3% of glucose and of glucose polymers having a DP less than or equal to 3 and less than 0.5% of glucose polymers having a DP greater than 600.

It is finally henceforth accepted by experts in the field of peritoneal dialysis that these glucose polymers, used for their osmotic power, are entirely satisfactory.

However, risks of microbial contamination of these preparations intended for peritoneal dialysis are to be deplored.

It is in fact known that glucose polymer production circuits can be contaminated with microorganisms, or with pro-inflammatory substances contained in said microorganisms.

The contamination of corn or wheat starches with microorganisms of yeast, mold and bacteria type, and more particularly with acidothermophilic bacteria of *Alicyclobacillus acidocaldarius* type (extremophilic bacteria which grow in the hot and acidic zones of the circuit) is, for example, described in the starch industry.

The major risk for the patient who receives these contaminated products is then peritonitis.

Clinical suspicion of peritonitis is diagnosed when there is a cloudy dialysate together with variable clinical manifestations, namely abdominal pain, nausea, vomiting, diarrhea and fever.

These episodes of peritonitis are caused by intraperitoneal bacterial infections, and the diagnosis usually easily established through positive dialysate cultures.

"Sterile peritonitis", which is also described as aseptic, chemical or culture-negative peritonitis, is, for its part, typically caused by a chemical irritant or a foreign body.

Since the introduction of icodextrin for the preparation of peritoneal dialysis solutions, isolated cases of aseptic peritonitis have been reported, that can be linked to various causes, and in particular induction by pro-inflammatory substances potentially present.

Aseptic inflammatory episodes are therefore major complications observed after injections of dialysis solutions.

While some of these inflammatory episodes are linked to a problem of chemical nature (accidental injection of chemical contaminants or incorrect doses of certain compounds), the majority of cases are directly associated with the presence of contaminants of microbial origin that are present in the solutions used to prepare the dialysis solutions.

Lipopolysaccharides (LPSs) and peptidoglycans (PGNs) are the main contaminants of microbial origin which present a high risk of triggering an inflammation when they are present in trace amounts.

The standard tests theoretically make it possible to discard batches which are loaded with contaminants of this type and which therefore present a health risk. However, these tests are not satisfactory, since aseptic inflammatory episodes are still reported, even though the solutions had been declared healthy.

Thus, despite the constant attention of those participating the field, in terms of reducing the risk of contaminations, in particular by improving detection thereof, there still remains a need to improve the performance levels of the detection of contaminants which can induce an inflammation.

DETAILED DESCRIPTION OF THE INVENTION

It is to the Applicant company's credit to have taken into account the presence of molecules capable of exacerbating the inflammatory response induced by other contaminants, in particular LPS or PGNs, especially via a mechanism of cooperation between TLRs (Toll-Like Receptors) and NOD (Nucleotide-binding Oligomerization Domain-containing protein)-like receptors. Indeed, to consider only the effect of the isolated contaminants on inflammation is reductive.

Contrary to LPS, which is a ligand recognized by receptors of TLR4 (Toll-Like Receptor) type, PGN (but also numerous glycolipids and lipopeptides) is a ligand recognized by receptors of TLR2 type which induces a weak inflammatory response in in vitro and in vivo models, thereby implying that these molecules must be present at higher concentrations in order to be detected.

Thus, in the models using mononuclear cells (PBMCs, primary monocytes/macrophages or monocyte lines), LPS induces a significant response for concentrations of about 1 ng/ml, whereas PGN concentrations at least 100 times higher are required to obtain a similar response (w/w ratio).

In addition, while soluble PGNs (MW≈125 kDa) induce an inflammatory response via the activation of TLR2, the depolymerization products thereof, the minimum structure of which is still bioactive is muramyl dipeptide (MDP), interact with NOD-like intracellular receptors.

These derivatives, considered in isolation, are not very inflammatory in vitro and give a significant response for values >1 µg/ml.

On the other hand, the presence of these molecules has a synergistic effect on the inflammatory response, by a mechanism of cooperation between TLRs and NOD-like receptors, regardless of the experimental model used (mouse, monocyte/macrophage lines, blood mononuclear cells).

In addition to the PGN depolymerization products, formylated microbial peptides, the prototype of which is f-MLP (formyl-Met-Leu-Phe tripeptide), also have a substantial synergistic activity. Originally, these peptides were identified for their chemoattractant activity on leukocytes, although they are incapable of inducing a cytokine response per se.

However, when they are combined with TLR agonists, they contribute to increasing cytokine production by sensitizing target cells.

It is therefore important not to ignore these "small molecules", since they can indirectly account for aseptic inflammatory episodes by exacerbating the effects of traces of PGN and/or of LPS.

Over the last few years, many tests using primary cells have been developed in order to replace animal models in inflammatory response tests.

However, these in vitro models are subject to considerable interindividual variability, which can be responsible for experimental biases.

Conversely, monocyte cell lines give constant responses, thereby explaining why the tests currently undergoing development increasingly use cells of this type in culture. However, these tests have the drawback of giving an overall inflammatory response to all the contaminants present as a mixture in a solution, and consequently do not make it possible to characterize the nature of the contaminant.

It is also important to note that the exacerbated inflammatory response is visible for cytokines of the acute phase of the inflammation, such as TNF-α (Tumor Necrosis Factor alpha), IL-1β (interleukin-1β) and chemokines such as CCL5 (Chemokine (C-C motif) ligand 5)/RANTES (Regulated upon Activation, Normal T-cell Expressed, and Secreted), but not or barely for IL-6 (interleukin 6). Thus, the methods based on the production of the latter (US2009/0239819 and US2007/0184496) are not suitable for detecting contaminants as a mixture in a solution.

Thus, the Applicant company has come to the following conclusions:

(i) it is difficult to detect bacterial contaminants present in trace amounts in biological solutions, (ii) it is important not to be limited to the detection of PGNs and of LPS, owing to the synergistic effects, (iii) it is necessary to develop new detection methods which are sensitive and reproducible, and (iv) it is advantageous to use sensitive and reproducible detection methods capable of characterizing the nature of the contaminants.

It is therefore to the Applicant company's credit to have developed sensitive and effective methods for detecting microbial contaminants which have a pro-inflammatory action, below the threshold of sensitivity of the procedures currently used and/or described in the literature, and subsequently for identifying the family, or even the nature, of the pro-inflammatory molecules present in trace amounts in the batches originating from the production circuits.

Indeed, a very sensitive method for measuring inflammatory responses in vitro will make it possible to retain or not retain batches on the basis of contamination levels which are "not significant", in the sense that these levels will be lower than the levels currently measurable using the standard tests.

It will be possible to propose these batches for making up the composition of solutions for therapeutic use in humans (e.g. peritoneal dialysis solutions).

Furthermore, the identification of the molecules responsible for the inflammatory responses shall make it possible to detect the sources of contaminations during production methods, and to introduce corrective modifications in order to reduce the levels of contaminants, or even eliminate them.

The method in accordance with the invention therefore relates to a method for detecting the pro-inflammatory contaminants of glucose polymers, in particular those for the preparation of a peritoneal dialysis solution, comprising an in vitro inflammatory response test.

The glucose polymers may be for peritoneal dialysis, enteral and parenteral feeding and the feeding of newborn babies. In one preferred embodiment, the glucose polymers that will be tested using the methods of the present invention are icodextrin or maltodextrins. They can be tested at one or more stages of their preparation, and in particular at the level of the raw material, at any step in their preparation process, and/or at the level of the final product of the process. They can also be tested as a sample of a peritoneal dialysis solution.

As previously mentioned, some molecules of bacterial origin, such as MDP and f-MLP, are weak inflammatory inducers, but they can act in combination or in synergy and increase the response induced by other contaminants.

This property is based on the fact that the molecules act via the intervention of receptors other than TLRs.

Besides LPS which reacts with TLR4, the majority of molecules with an inflammatory potential that may be present in the batches are TLR2 agonists.

These contaminants are difficult to detect, since they are present in low concentrations and the inflammatory response that they will trigger is most commonly close to the background noise.

Consequently, the presence of molecules with synergistic activity can exacerbate the inflammatory response induced by TLR2 ligands, which can be taken advantage of for detecting low doses of contaminants.

Samples contaminated with MDP (NOD2 agonist), f-MLP (microbial peptide receptor ligand), or even with LPS (for triggering TLR4/TLR2 synergy) will as a result trigger an in vitro inflammatory response.

Thus, the pro-inflammatory contaminants detected by means of the method of the invention are capable of triggering, separately or in combination, an inflammatory reaction. In particular, these contaminants may be weak inflammatory inducers when they are considered separately, but may induce a substantial inflammatory reaction when they are in combination. The method according to the invention makes it possible to consider the effect of the set of contaminants present in the glucose polymer preparation under consideration and not only the particular effect of each of them.

The method according to the invention comprises at least one in vitro inflammatory response test using a cell line which makes it possible to detect at least one inflammatory response factor. Preferably, the cell line is either a macrophage or a macrophage-differentiated cell line, or a cell expressing one or more TLRs or NOD-like receptors such as TLR2, TLR4 or NOD2, or a combination thereof.

According to a first embodiment, the cell line used in the inflammatory response test is a macrophage or a macrophage-differentiated cell line. In particular, the cell line produces TNF-α and the chemokine CCL5/RANTES. Preferably, the test is carried out with macrophage-differentiated THP-1 cells.

In one preferred embodiment, the macrophages or macrophage-differentiated cells, in particular the macrophage-differentiated THP-1 cells, are used at a density of between 0.5 and $1 \times 10^6$ cells/ml of culture medium, preferably between 0.7 and $0.8 \times 10^6$ cells/ml, and even more preferably approximately $0.75 \times 10^6$ cells/ml.

The in vitro inflammatory response test can be based on the production of TNF-α and/or of the chemokine CCL5/RANTES by macrophages, in particular macrophage-differentiated THP-1 cells, given that the synergistic effect (effect obtained via the combination of these various contaminants) is especially marked for the cytokines of the acute phase of inflammation (TNF-α, IL-1β, chemokines), but not for cytokines of the delayed phase, such as IL-6.

Thus, according to one particular embodiment, the inflammatory response test consists in placing the cells of the cell line, preferably macrophages, in the presence of a preparation of glucose polymers that may contain pro-inflammatory contaminants and in measuring the production of cytokines of the acute phase of inflammation, in particular TNF-α, IL-1β and/or chemokines, in particular CCL5/RANTES, the production of these cytokines indicating that the preparation contains contaminants capable of triggering an inflammatory reaction. In one particularly preferred embodiment, the test comprises measuring the production of TNF-α and/or of CCL5/RANTES, preferably of CCL5/RANTES. The cytokine assays can be carried out by any means well known to those skilled in the art, and in particular by ELISA. In one preferred embodiment, the test comprises measuring the production of TNF-α after 8 h of stimulation. In another preferred embodiment, the test comprises measuring the production of RANTES after 20 h of stimulation, in particular by means of an ELISA assay.

In order to increase the cell response induced by pro-inflammatory contaminants, for example by LPSs and/or PGNs, a component which makes it possible to act in synergy with the contaminants can be added to the test sample. Indeed, this can make it possible to detect lower doses of contaminants. Preferably, this component may be MDP or a related molecule (N-glycolyl-MDP, L18-MDP), a formylated microbial peptide (f-MLP), or LPS. Preferably, this component is MDP, f-MLP or LPS. Even more preferably, this component is MDP or LPS. In particular, the LPS is an *E. coli* LPS.

In one preferred embodiment, MDP, in particular *S. aureus* MDP, is added to the sample. Preferably, the MDP is added to the sample at a concentration of more than 1 µg/ml, preferably at a concentration of between 1 and 100 µg/ml. In one most particularly preferred embodiment, the MDP is added to the sample at a concentration of 10 µg/ml.

In another preferred embodiment, the f-MLP is added to the sample at a concentration of more than 10 nM, preferably of at least 50, 100, 150, 200, 300, 400 or 500 nM.

In yet another preferred embodiment, the LPS, in particular an *E. coli* LPS, can be added to the sample at a concentration of at least 10 pg/ml, for example at a concentration of 25 pg/ml.

In one preferred embodiment, the glucose polymer preparation tested has a glucose polymer concentration of from 5 to 50 mg/ml, preferably between 5 and 10, 20, 30 or 40 mg/ml. In one particular embodiment, the glucose polymer preparation tested has a glucose polymer concentration of approximately 5 mg/ml. In one preferred embodiment, the glucose polymer preparation tested has a glucose polymer concentration of approximately 25 mg/ml.

Optionally, a sample of the glucose polymer preparation can be treated with a mutanolysin prior to the test. This enzyme, through its muramidase activity, is capable of depolymerizing PGNs. For example, the enzyme at a concentration of approximately 2500 U/ml can be placed in the presence of the sample, optionally diluted so as to have a glucose polymer concentration of from 7.5 to 37.5% (weight/volume), for 6 to 16 h, preferably approximately 16 h. The sample thus treated will then be subjected to the test with macrophages according to the present invention. Optionally, the result, i.e. the cytokine production, obtained with the sample treated with a mutanolysin may be compared with the result obtained without treatment.

Optionally, in another alternative, the sample of the glucose polymer preparation can be filtered prior to the test. The purpose of this filtration is essentially to remove the high-molecular-weight molecules, such as the high-molecular-weight PGNs, and to perform the test on the filtrate in order to analyze most particularly the contaminants of small sizes. The cut-off threshold for the filtration can, for example, be between 30 kD and 150 kD, preferably between 30 and 100 kD or between 30 and 50 kD, and in particular approximately 30 kD. Preferably, the filtration is carried out by ultrafiltration. It can also be carried out by any means known to those skilled in the art. Thus, the sample thus filtered, the filtrate, will be subjected to the test with macrophages according to the present invention. Optionally, the result, i.e. the cytokine production, obtained with the filtrate may be compared with the result obtained without or before filtration. This will make it possible to deduce the specific inflammatory contribution of the molecules of small sizes.

In one preferred and particular embodiment, the method has one or more of the following characteristics:
- the cell line is used at a density of between 0.5 and $1 \times 10^6$ cells/ml, preferably between 0.7 and $0.8 \times 10^6$ cells/ml, and even more preferably approximately $0.75 \times 10^6$ cells/ml; and/or
- the glucose polymer concentration is less than 50 mg/ml, preferably approximately 25 mg/ml; and/or
- the cytokine production is measured after 20 h of stimulation for RANTES and/or 8 h of stimulation for TNF-α; and/or
- MDP is added, to the glucose polymer preparation, at a concentration of between 1 and 100 µg/ml, preferably approximately 10 µg/ml.

Preferably, the method comprises all the characteristics. Thus, in one very particular mode, the method comprises:
- placing macrophages in the presence, for approximately 20 h, of a preparation of glucose polymers that may contain pro-inflammatory contaminants in the presence of MDP, preferably at a concentration of between 1 and 100 µg/ml, the glucose polymer concentration being less than 50 mg/ml, preferably approximately 25 mg/ml, and the macrophages having a density of between 0.5 and $1 \times 10^6$ cells/ml, preferably between 0.7 and $0.8 \times 10^6$ cells/ml, and even more preferably approximately $0.75 \times 10^6$ cells/ml; and
- measuring the production of CCL5/RANTES, the production of CCL5/RANTES indicating that the preparation contains contaminants capable of triggering an inflammatory reaction.

Quite particularly, this first embodiment makes it possible to detect the contamination of the glucose polymer with PGNs and/or LPS, preferably with medium-sized PGNs (in particular of approximately 120 kDa) and/or LPS, even more particularly with LPSs.

In particular, the method can comprise the quantification of the contaminants. For example, this quantification can be carried out using a dose-response curve. This dose-response curve can in particular be produced with the same cells, under the same conditions, with increasing doses of contaminants. Preferably, such a dose-response curve can be produced with increasing doses of LPS.

This first embodiment can be implemented in the methods according to the present invention alone or in combination with a second embodiment.

According to the second embodiment, the cell line used to carry out the in vitro inflammation test is a line which makes it possible to detect the activity of one or more innate immunity receptors.

In particular, this cell line can be obtained by stable transfection with one or more vectors encoding one or more innate immunity receptors.

The activity of an innate immunity receptor can be detected, for example, by using a reporter gene which is under the direct control of the signaling pathway associated with said receptor. Preferably, this reporter gene encodes a colored or fluorescent protein or encodes a protein of which the activity can be measured with or without a substrate. In particular, the reporter gene encodes an alkaline phosphatase.

Thus, the method comprises placing one or more cell lines expressing one or more TLRs or NOD-like receptors in the presence of the preparation of glucose polymers and measuring the activity of the receptors, in particular by means of the signal of a reporter gene.

This reporter gene signal indicates the presence in the preparation of a contaminant which is an agonist of the receptor.

Preferably, the cell line makes it possible to detect the activity of one or more TLRs or NOD-like receptors, such as the TLR2, 3, 4, 5, 7, 8 or 9 or NOD2 receptors. Preferably, the cell line makes it possible to detect the activity of one or more receptors chosen from TLR2, TLR4 and NOD2. In one particular embodiment, the cell line expresses the TLR2, TLR4 and NOD2 receptors and makes it possible to detect their activity.

The cell lines used may, for example, be HEK-BLUE lines (sold by the company InvivoGen), modified by stable transfection with vectors encoding innate immunity receptors. However, it should be noted that those skilled in the art can also use other commercially available lines (Imgenex) or they can prepare them.

These cells can also be cotransfected with a reporter gene producing, for example, a secreted form of alkaline phosphatase (SEAP: secreted embryonic alkaline phosphatase), the synthesis of which is under the direct control of the signaling pathway associated with the receptor(s) expressed in the same cell line. In one preferred embodiment, the enzymatic reaction is carrying out using a 1:3 ratio of test medium versus SEAP reagent (for example, 50 µl of medium and 150 µl of SEAP reagent). In addition, a reaction time of at least 60 minutes will be preferred.

The cell lines can, for example, be chosen from the group consisting of:
the HEK-BLUE hTLR2 line (line which responds specifically to TLR2 agonists), the HEK-BLUE hNOD2 line (line which responds effectively to PGN depolymerization products and to related molecules (MDP, L18-MDP, etc.), and the RAW-BLUE line (mouse macrophage line transfected so as to express an alkaline phosphatase). The RAW-BLUE line expresses innate immunity receptors, and particularly the TLR2, TLR4 and NOD2 receptors.

These lines are detailed later in this description.

In one preferred embodiment, a line expressing TLR2 and making it possible to detect its activity, and/or a line expressing the TLR2, TLR4 and NOD2 receptors and making it possible to detect their activity will be used. By way of example, the HEK-BLUE hTLR2 and/or RAW-BLUE cell lines will be used. Most particularly, the method will implement a test using the HEK-BLUE hTLR2 and RAW-BLUE cell lines.

In another preferred embodiment, two lines expressing respectively TLR2 and NOD2 and making it possible to detect their activity (separately), and one line expressing the TLR2, TLR4 and NOD2 receptors and making it possible to detect their activity will be used. By way of example, the HEK-BLUE hTLR2, HEK-BLUE hNOD2 and RAW-BLUE cell lines will be used. Most particularly, the method will implement a test using the HEK-BLUE hTLR2, HEK-BLUE hNOD2 and RAW-BLUE cell lines.

The use of such lines therefore makes it possible to replace the cytokine assays with an enzymatic test (phosphatase activity), and to target certain families of molecules of bacterial origin according to the receptor(s) expressed by the line.

In addition, these lines make it possible to detect contaminants at very low thresholds, in particular for TLR2 agonists (PGN, LTA (lipoteichoic acid), LM (Lipomannan), etc.) and NOD2 agonists (PGN depolymerization products and MDP). Thus, the line expressing NOD2, in particular HEK-BLUE hNOD2, makes it possible most particularly to detect a contamination with PGN depolymerization products and MDP, preferably MDP. The line expressing TLR2, in particular HEK-BLUE hTLR2 and/or RAW-BLUE, makes it possible most particularly to detect a contamination with PGNs.

According to this second embodiment, the in vitro inflammatory response test consists in placing the cells of the cell line making it possible to detect the activity of one or more innate immunity receptors in the presence of a preparation of glucose polymers that may contain pro-inflammatory contaminants and in measuring the activity of the receptor or of the signal of the reporter gene that is associated therewith.

The detection of this activity or of this signal indicates that the preparation contains contaminants capable of activating one or more innate immunity receptors and of triggering an inflammatory reaction.

In one preferred embodiment, the glucose polymer preparation tested has a glucose polymer concentration of from 5 to 50 mg/ml, preferably between 5 and 10, 20, 30 or 40 mg/ml. In one particular embodiment, the glucose polymer preparation tested has a glucose polymer concentration of approximately 5 mg/ml. In the preferred embodiment, the glucose polymer preparation tested has a glucose polymer concentration of approximately 37.5 mg/ml when HEK-BLUE hTLR2 and/or HEK-BLUE hNOD2 cells are used. In another preferred embodiment, the glucose polymer preparation tested has a glucose polymer concentration of approximately 50 mg/ml when RAW-BLUE cells are used.

Optionally, a sample of the glucose polymer preparation can be treated with a mutanolysin prior to the test. This enzyme, through its muramidase activity, is capable of depolymerizing PGNs. For example, the enzyme at a concentration of 2500 U/ml can be placed in the presence of the sample, optionally diluted so as to have a glucose polymer concentration of from 7.5% to 37.5% (weight/volume), for 6 to 16 h, preferably approximately 16 h. The sample thus treated will then be subjected to the methods according to the second embodiment. Optionally, the result obtained with the sample treated with a mutanolysin may be compared with the result obtained without treatment.

Optionally, in another alternative, the sample of the glucose polymer preparation can be filtered prior to the test. The purpose of this filtration is essentially to remove the high-molecular-weight molecules, such as the high-molecular-weight PGNs, and to carry out the test on the filtrate in order to analyze most particularly the contaminants of small sizes. The cut-off threshold for the filtration can, for example, be between 30 kD and 150 kD, preferably between 30 and 100 kD or between 30 and 50 kD, and in particular approximately 30 kD. Preferably, the filtration is carried out by ultrafiltration. It can also be carried out by any means known to those skilled in the art. Thus, the sample thus filtered, the filtrate, will be subjected to the methods according to the second embodiment. Optionally, the result obtained with the filtrate may be compared with the result obtained without or before filtration. This will make it possible to deduce the specific inflammatory contribution of the molecules of small sizes.

In one preferred and particular embodiment of this second embodiment, the method has one or more of the following characteristics:

the cell line is used at a density of approximately 50 000 cells/well for a 96-well plate and for HEK-BLUE hTLR2 or RAW-BLUE and of 10 000 cells/well for a 96-well plate for HEK-BLUE hNOD2; and/or the glucose polymer preparation tested has a glucose polymer concentration of from 5 to 50 mg/ml, preferably a glucose polymer concentration of approximately 37.5 mg/ml when HEK-BLUE hTLR2 and/or HEK-BLUE hNOD2 cells are used and a glucose polymer concentration of approximately 50 mg/ml when RAW-BLUE cells are used; and/or the bringing of the glucose polymer preparation into contact with the cells lasts approximately 16 to 24 h; and/or the signal of the SEAP reporter gene is detected with a culture supernatant:SEAP substrate ratio of 20:180, preferably of 50:150, preferably after at least 60 minutes of incubation, ideally 60 minutes.

In one particular embodiment, the method comprises all the characteristics.

In particular, the method may comprise the quantification of the contaminants. For example, this quantification can be carried out using a dose-response curve. This dose-response curve can in particular be produced with the same cells, under the same conditions, with increasing doses of contaminants. Preferably, such a dose-response curve can be produced for the cells expressing TLR2 (for example, HEK-BLUE hTLR2 and RAW-BLUE) with increasing doses of PGN and for the cells expressing NOD2 (for example, HEK-BLUE hNOD2) with increasing doses of MDP.

The method according to the invention can thus also comprise a step consisting in identifying the contaminant(s) capable of triggering an inflammatory reaction.

For this, a cell line making it possible to detect the activity of an innate immunity receptor or several innate immunity receptors, as described above, is placed in the presence of the glucose polymer preparation to be tested. The activity of the receptor or the signal of the reporter gene associated with this receptor is measured. The detection of this activity or of this signal indicates the presence, in the preparation, of a contaminant which is an agonist of the receptor.

Thus, the line expressing NOD2, in particular HEK-BLUE hNOD2, makes it possible most particularly to detect a contamination with PGN depolymerization products and MDP, preferably MDP. The line expressing TLR2, in particular HEK-BLUE hTLR2 and/or RAW-BLUE, makes it possible most particularly to detect a contamination with PGNs. Moreover, the macrophages, in particular the THP-1 macrophages, make it possible most particularly to detect a contamination with LPSs.

According to one embodiment, the method according to the invention comprises the steps consisting of:

(a) carrying out at least one in vitro inflammatory response test, as described above in the first embodiment, consisting in placing the cells of a cell line, preferably macrophages, in the presence of a preparation of glucose polymers that may contain pro-inflammatory contaminants and in measuring the production of cytokines of the acute phase of inflammation, in particular TNF-α, IL-1β and/or chemokines such as CCL5/RANTES, the production of these cytokines indicating that the preparation contains contaminants capable of triggering an inflammatory reaction, and/or (b) placing a cell line which makes it possible to detect the activity of an innate immunity receptor or several innate immunity receptors, as described above in the second embodiment, in the presence of the preparation and detecting the activity of the receptor or the signal of the reporter gene associated with this receptor, the detection of this activity or of this signal indicating the presence, in the preparation, of a contaminant which is an agonist of the receptor.

According to one preferred embodiment, the method according to the invention comprises the steps consisting of:

(a) carrying out at least one in vitro inflammatory response test consisting in placing the cells of a cell line, preferably macrophages, in the presence of a preparation of glucose polymers that may contain pro-inflammatory contaminants and measuring the production of cytokines of the acute phase of inflammation, in particular TNF-α, IL-1β, and/or chemokines such as CCL5/RANTES, the production of these cytokines indicating that the preparation contains contaminants capable of triggering an inflammatory reaction, and (b) when the preparation contains contaminants, placing a cell line which makes it possible to detect the activity of an innate immunity receptor or several innate immunity receptors, as described above, in the presence of the preparation and detecting the activity of the receptor or the signal of the reporter gene associated with this receptor, the detection of this activity or of this signal indicating the presence, in the preparation, of a contaminant which is an agonist of the receptor.

Steps a) and b) of this method are carried out according to the details provided above. Preferably, the method comprises the two steps.

In one preferred embodiment, a cell line expressing the TLR2 receptor and making it possible to detect its activity, such as HEK-BLUE hTLR2, and/or a line expressing several innate immunity receptors, as described above, in particular TLR2, TLR4 and NOD2, such as RAW-BLUE, will be used. Most particularly, the method will implement a test using the HEK-BLUE hTLR2 and RAW-BLUE cell lines.

In another preferred embodiment, a cell line expressing the TLR2 receptor and making it possible to detect its activity, such as HEK-BLUE hTLR2, a cell line expressing the NOD2 receptor and making it possible to detect its activity, such as HEK-BLUE hNOD2 and/or a line expressing several innate immunity receptors, as described above, in particular TLR2, TLR4 and NOD2, such as RAW-BLUE, will be used. Most particularly, the method will implement a test using the HEK-BLUE hTLR2, HEK-BLUE hNOD2 and RAW-BLUE cell lines.

This method therefore makes it possible not only to detect the presence of pro-inflammatory contaminants in a glucose polymer preparation, but also to obtain information on the nature of these contaminants. It is in particular possible to define whether these contaminants are agonists of TLRs or NOD-like receptors, such as TLR2, TLR4 or NOD2. According to one preferred embodiment, several lines can be used to provide information additional to that obtained, for example, with the cytokine response tests in the differentiated THP-1 cells:

HEK-BLUE hTLR4 line: this line responds specifically to TLR4 agonists. It makes it possible in particular to assay LPSs;

HEK-BLUE hTLR2 line: this line responds specifically to TLR2 agonists. It makes it possible in particular to assay PGNs.

Its use therefore makes it possible to determine the contribution of these contaminants in the triggering of inflammatory responses.

In one particular embodiment, the sample of the glucose polymer preparation can be filtered as described above, preferably with a cut-off threshold of 30 kDa, in particular by ultrafiltration, in order to remove the PGNs, in particular the PGNs of large size. Thus, the lipopeptides and glycopeptides of small size, which are other TLR2 agonists, are retained in the filtrate and only their response will be measured by testing the filtrate.

In addition, treatment of the solutions with lysozyme and/or β-glucanase makes it possible to eliminate the PGN and/or the β-glucans, and to thus determine the significance of the other TLR2 agonists that may be present in the contaminated batches (glycolipids and lipopeptides). Moreover, a sample of the glucose polymer preparation can be treated with a mutanolysin prior to the test, in particular as detailed above;

the HEK-BLUE hNOD2 line: this line responds specifically to NODS agonists. It makes it possible in particular to assay MDPs.

The use of this line therefore makes it possible to detect them at low concentrations. This analysis is all the more advantageous since the presence of PGN implies that its degradation products are also present, and that they can act synergistically with the TLR agonists;

HEK-BLUE Null2 line: this is a control line, the use of which is necessary in order to verify that the glucose polymer solutions do not induce the production of the enzyme via an intrinsic mechanism;

RAW-BLUE line: this is a mouse macrophage line transfected with SEAP.

The advantage of this line is that it naturally expresses virtually all the innate immunity receptors.

It serves as a positive control in the tests, since it is supposed to respond to microbial contaminants of any type.

A subject of the invention is also the means for identifying the pro-inflammatory contaminants.

LPS and PGN assays can be carried out by any means known to those skilled in the art. For example, the peptidoglycan content can be determined according to two tests:

standard SLP test sold by the company WAKO Pure Chemical Industries Ltd.,

SLP-HS test, high-sensitivity test developed and validated by the Applicant company as detailed in its patent application WO 2010/125315.

These tests have different reagents (SLP reagents, PGN standards) exhibiting biological reactivities to substantially different PGN impurities, and thus different performance criteria:

Standard SLP test: SLP reagent n° 297-51501-*Micrococcus luteus* PGN standard n° 162-18101.

SLP-HS (high sensitivity) test: SLP-HS kit n° 293-58301 (including a *Staphylococcus aureus* PGN standard).

The SLP-HS method developed by the Applicant company is more sensitive. It has limits of detection (LD) and limits of quantification (LQ) below the standard SLP method:

SLP-HS test LD of 1 ng/g and LQ of 3 ng/g.

Standard SLP test LD of 20 ng/g and LQ of 40 ng/g.

Thus, unless otherwise arranged, the assaying of PGNs according to conventional methods is carried out in the present application using the SLP-HS test, since, as will be exemplified hereinafter and described below, the SLP-*HS test is more sensitive than the standard SLP test.

The "inflammatory response" tests as described above, for example using the HEK-BLUE cells, make it possible to identify the nature of the main contaminants (LPS, PGN, β-glucans. MDP and related molecules) and to estimate their contribution in the induction of the inflammatory response.

The other contaminants that may be present in the test batches are essentially glycolipids and lipopeptides which are TLR2 agonists, or microbial peptides;

for the glycolipids and lipopeptides, a fractionation procedure based on their amphiphilic nature is carried out in order to recover them and concentrate them.

Treatment with a chloroform/methanol mixture makes it possible to extract these molecules from the glucose polymer solutions and to concentrate them after evaporation of the chloroform.

Once the molecules have been recovered, they are taken up in a minimum volume of DMSO (or any other solvent that is nontoxic for the cells) and then analyzed in the inflammatory response tests previously described.

Thus, the use of a cell line which makes it possible to detect the activity of a receptor such as TLR2, for example the HEK-BLUE hTLR2 line, makes it possible to confirm the presence or absence of traces of TLR2 agonists other than the PGN in the batches to be analyzed.

The compounds can also be tested in a model using cells expressing all the types of receptors, such as the RAW-BLUE cells, but, in this case, the glucose polymer solutions are pretreated on DETOXI-GEL, so as to remove the traces of LPS.

Depending on the amounts recovered, a finer analysis of the contaminants is carried out.

In particular, the sample can be filtered. For example, the sample of the glucose polymer preparation can be filtered with a cut-off threshold of 30 kDa, in particular by ultrafiltration. This makes it possible to remove the PGNs, in particular the PGNs of large size. Thus, the lipopeptides and the glycopeptides of small size, which are other TLR2 agonists, are retained in the filtrate and the filtrate can be analyzed in order to determine the nature of the contaminants.

Moreover, treatment with the chloroform/methanol mixture makes it possible to extract the products which are subsequently fractionated on C18 resin and/or a carbon column. The compounds are then eluted using a water/acetonitrile gradient. Depending on the purity of the fractions and on the amount of material, a more fine analysis makes it possible to determine the biochemical nature of these compounds, or even their structure.

For the microbial peptides, an ultrafiltration step on a 5 kDa filter makes it possible to extract them from the glucose polymer solutions. If necessary, passing over a carbon column makes it possible to rid the filtrate of the more hydrophobic compounds of size <5 kDa.

The solutions are subsequently concentrated and then tested for their biological properties. Since these peptides are chemoattractants for leukocytes, their presence can be detected in an in vitro cell migration test available in the laboratory.

It may be that the glucose polymers are contaminated with other molecules known to trigger inflammatory responses, such as flagellin, which is a TLR5 agonist protein, and derivatives of nucleic acids and related molecules, agonists of TLR3, 7, 8 and 9 (the first three are involved in reactions to compounds of viral origin, while TLR9 is activated by DNA of bacterial origin).

In this case, the cell lines which make it possible to detect the activity of these various TLRs, in particular HEK-BLUE lines, are available and can be used to analyze the impact of these molecules in inflammatory responses.

Furthermore, the presence of oligonucleotide compounds can be confirmed or otherwise by biochemical analyses.

The method of the invention allows the detection of the contaminants of glucose polymers for peritoneal dialysis, said contaminants being capable of acting in synergy with one another in order to trigger an inflammatory reaction, characterized in that it comprises at least one in vitro inflammatory response test using modified cell lines.

In one particular embodiment, the present invention also provides a method for quantifying the PGNs in a sample, in particular of glucose polymers for peritoneal dialysis, which comprises incubating the sample with a cell line which makes it possible to detect the activity of the TLR2 receptor and measuring the activation of the signaling pathway associated with TLR2, thus making it possible to determine the amount of PGN contained in the sample.

In particular, this line is a line modified by transfection (preferably stable transfection) with a vector encoding the TLR2 receptor. Preferably, this line does not express other innate immunity receptors. In addition, this line may contain a reporter gene which is under the direct control of the signaling pathway associated with the TLR2 receptor. Preferably, this reporter gene encodes a colored or fluorescent protein or encodes a protein of which the activity can be measured with or without substrate. In particular, the reporter gene encodes an alkaline phosphatase. These cells can, for example, be cotransfected with a reporter gene producing, for example, a secreted form of alkaline phosphatase (SEAP: secreted embryonic alkaline phosphatase), the synthesis of which is under the direct control of the signaling pathway associated with the TLR2 receptor. This line can, for example, be the HEK-BLUE hTLR2 line.

In order to determine the amount of PGN contained in the sample on the basis of measuring the activation of the signaling pathway associated with TLR2, a dose-response curve is simultaneously established with a calibration range comprising increasing concentrations of PGN, preferably of *S. aureus* PGN.

Prior to the assay, the sample to be assayed can optionally have been partially purified in order to remove, for example, any bothersome contaminants. Glycopeptides and lipopeptides can be removed from the sample by chloroform extraction. After centrifugation, the assay will be carried out on the aqueous phase, from which the contaminants of lipophilic nature have normally been removed. Fractionation on a microconcentrator, on filters with 30 or 50 kDa thresholds, can be carried out, the assay then being carried out on the retentate. Prior treatment with β-glucanase can make it possible to refine the assay by eliminating the related molecules.

Alternatively and preferably, the sample to be assayed is treated prior to the assay with a mutanolysin. For example, the enzyme at a concentration of approximately 2500 U/ml can be placed in the presence of the sample, preferentially diluted so as to have a glucose polymer concentration of from 7.5% to 37.5% (weight/volume) if this is necessary. The treatment can last for 6 to 16 h, preferably for approximately 16 h. In the preferred embodiment, the treatment is carried out for approximately 16 h at approximately 37° C. on a sample having a glucose polymer concentration of approximately 7.5% (weight/volume). The sample thus treated will then be brought into contact with cells expressing TLR2, in particular HEK-BLUE hTLR2 cells. Optionally, the result obtained with the sample treated with a mutanolysin may be compared with the result obtained without treatment.

This same method can also be carried out for detecting the contaminants of glucose polymers for enteral and parenteral feeding, or even for the feeding of newborn babies.

The invention will be understood more clearly by means of the examples which follow, which are meant to be illustrative and nonlimiting.

BRIEF DESCRIPTION OF THE FIGURES

FIG. 21A, theoretical curve. FIG. 21B, curve obtained with HEK-BLUE-hTLR2 cells.

EXAMPLE 1

Figure 1:
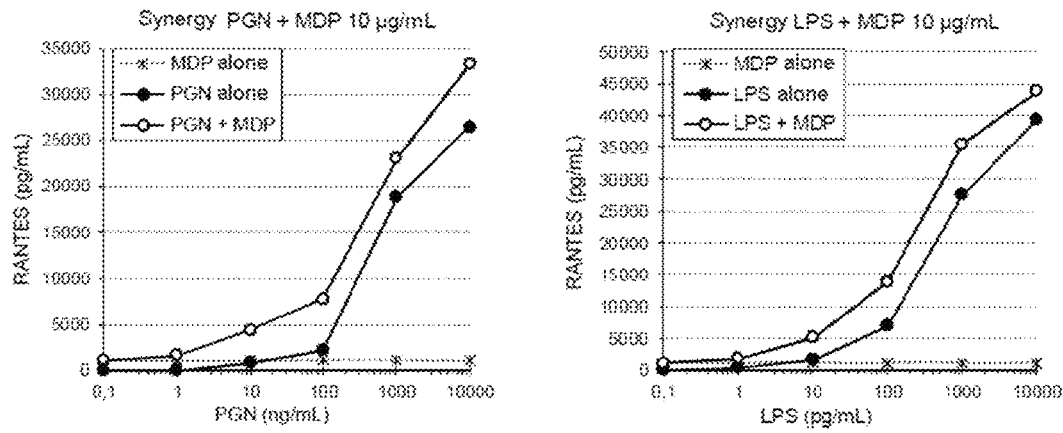
FIG. 1: Production of RANTES in response to the PGN and to the LPS in THP-1 cells sensitized with MDP at 10 µg/ml.

Preparation of the Glucose Polymers for Peritoneal Dialysis

The raw material for obtaining the glucose polymers according to the invention is produced from waxy corn starch in the following way:
cleaning of the corn so as to keep exclusively the whole corn grains,
steeping of the corn thus cleaned, in the presence of lactic acid so as to soften the grains,
wet milling, then separation of the various constituents, i.e. germ, cellulose husk, proteins and starch,
cleaning of the starch in countercurrent mode with purified water so as to purify the starch both physicochemically and bacteriologically,
centrifugation and drying of the starch,
suspension of the starch in purified water at a final dry matter content of 40% and at a temperature of 45° C. to 50° C.,
acidification of the starch suspension by addition of HCl at a pH <2, and raising of the temperature to 115 to 120° C. for 6 to 8 minutes,
flocculation of the proteins and of the fats at this pH, neutralization of the suspension at pH 5, filtration of the suspension through diatomaceous earth (so as to retain the residual proteins, fats and cellulose), demineralization on strong cationic resin and weak anionic resin, treatment with activated carbon at a temperature of 70-80° C. and at a pH of from 4 to 4.5; which removes the colored impurities and reduces the level of microbiological impurities.

The activated carbon powder which is added at a concentration between 0.2% and 0.5% on a dry basis is retained on a 10 μm ceramic filter loaded beforehand with a filtering agent, concentration by passing through a falling film evaporator, spray-drying of the concentrated solution in an MSD spray dryer sold by the company Niro.

This starch hydrolysate complies with the monograph of the European Pharmacopeia (ref Maltodextrins: 1542).

pH: 4.0-7.0 for a solution at 10%,

I.d.: complies,

Loss on drying: 6% max,

DE: <20

Sulfated ash: 0.5% max $SO_2$: 20 ppm max

Heavy metals: <10 ppm

*E. coli*: absent/g

Salmonellae: absent/10 g

Total viable microorganisms: 100 CFU/g max (EP 1000 CFU/g)

Molds: 100 CFU/g max

In addition to this, the batches produced are analyzed on the basis of the values of:

yeast+mold contamination: 150 CFU/10 g max, i.e. 15/g max aerobic microorganisms: 500 CFU/10 g max, i.e. 50/g max endotoxins (endpoint gel clot LAL test): 20 EU/g max peptidoglycans: 2700 ng/g max The conditions for obtaining the glucose polymers in accordance with the invention from the starch hydrolysate thus obtained are the following:

1) Water Preparation/Water Quality purification of the water by filtration through 3 μm; treatment on activated carbon, demineralization on cations and anion exchange resins, and filtration again (UA), two tanks used:

10 m³ for dissolving the starch hydrolysate, and the spray-dry rinsing and cleaning steps, 60 m³ for the main process (cleaning of the tanks, its suspensions of activated carbon and chromatography).

3) Chromatography solubilization of the starch hydrolysate with purified water so as to obtain a dry matter content of 35-45% at a temperature between 60-85° C., sterilizing filtration of the starch hydrolysate by passing it through 0.45 μm and then 0.22 μm, carried out at a ΔP<3 bar, size exclusion chromatography (SEC) separation carried out using a continuous system composed of six series of double plates, each of 1 m³ of resin. The resin used is a PCR145K sold by the company PUROLITE.

The solution which passes through this resin has a temperature between 75 and 85° C. at 35-45% dry matter content.

The duration of each sequence defines the process.

In the present case, the duration of each sequence is 15 minutes.

The control is carried out by analysis of molecular weight distribution and analysis of the chromatography yield, in the following way: (Amount of dry matter of the desired fraction)/(Amount of dry matter of the feed).

The lowest molecular weights interact with the resin and the high molecular weights are eluted with purified water.

The concentration is carried out by falling film evaporation at a dry matter content of 35-45%.

A heat treatment is carried out at a temperature of 120° C. for 2 minutes.

Activated carbon is added between 0.5% and 1.5% of the total weight of the starch hydrolysate at 75° C. with cationic resins (1 to 3 l) for controlling the pH (4-4.5) and anionic resins (5 to 10 l) for controlling the pH (5.5-6).

Filtration is carried out through polypropylene bag filters with ΔP<5 bar, in 5 to 6 hours per batch.

A second and third filtration through 1.5 and 0.45 μm, and then through 0.22 and 0.1 μm, and ultrafiltration through a membrane with a cut-off threshold of about 40 000 Da are carried out.

For the spray-drying: feed at 500 kgs/h with a solution at 40% dry matter content and at 250° C. in an MSD spray dryer sold by the company Niro.

The spray-dried product has, on exiting, a moisture content of less than 6%.

The product is then cooled in a fluidized air bed comprising three cooling zones fed with air at 40, 30 and 20° C. The product obtained is then sieved through 800 μm in order to remove the aggregates.

About 500 kgs of final product are obtained from 800 kgs of starting maltodextrins, i.e. a yield of about 60%.

The determination of the possible contamination of the circuit is carried out by analysis of the peptidoglycan and endotoxin content on the final product.

For example, the contents usually observed and measured on the batches of the final product (expressed per g of glucose polymer) are, for the criteria specified above, the following:

Yeasts and molds: 0/g

Aerobic microorganisms: 0/g

Endotoxins (endpoint gel clot LAL test): 0.3 EU/g

Peptidoglycans: <3 ng/g

*B. acidocaldarius*: 1/g

EXAMPLE 2

Use of the "Sensitized" THP-1 Cell Line for Detecting Pro-Inflammatory Contaminants Materials & Methods The THP-1 cells (88081201, ECACC) are cultured routinely in the laboratory.

For the pro-inflammatory activation experiments, the THP-1 cells are differentiated for 3 days in the presence of phorbol ester (PMA). In particular, the cells are placed in culture in 200 μl of complete medium in the presence of 20 nM of PMA for 72 h (final cell density: $0.75 \times 10^6$ cells/ml).

The glucose polymer samples are prepared according to example 1.

TABLE 1

| | \multicolumn{8}{c}{Glucose polymer samples} | | | | | | | |
|---|---|---|---|---|---|---|---|---|
| | I-10.01 | I-10.02 | I-10.03 | I-11.12 | MM-10.04 | MM-10.05 | MP-10.06 | MP-10.07 |
| LAL Test (EU/g) | <0.3 | 0.3 | <0.3 | 0.6 | 1.2 | 9.6 | <0.3 | 38.4 |
| Standard SLP Test (ng/g) | <20 | 755 | 27 | 530 | <20 | 2755 | <20 | 4613 |
| SLP-HS Test (ng/g) | <3 | 253 | 12 | 393 | <3 | 501 | <3 | 645 |

The standard molecules for establishing the calibration ranges are, for the:
LAL test: *E. coli* O55B5 LPS
Standard SLP test: *M. luteus* PGN—Wako
SLP-HS test: *S. aureus* PGN—Wako.

The assayed PGN values differ from one Wako test to another owing to the different reactivity and sensitivity of these tests and potentially to their limited and relative specificity (in particular, possible response to β-glucans).

The optimization studies are carried out with I-10.01 glucose polymer solutions (table 1) artificially loaded with standard inflammatory molecules: PGN and MDP (source: *S. aureus*), LPS (source: *E. coli*), f-MLP (synthetic peptide).

The solution for dilution of the standards is I-10-01 with <0.3 EU/g of LPS (LAL test), <20 ng/g of PGN (standard SLP test) and <3 ng/g (SLP-HS test) and used at the final concentration of 5 mg/ml.

The analyses are then carried out on a first series of samples corresponding to various batches selected on the basis of the levels of contamination with impurities measured using the LAL and SLP tests (PGN, LPS and β-glucans).

The ELISA kits for assaying TNF-α and CCL5/RANTES are purchased from AbCys, the standard agonists (PGN, LPS, f-MLP and MDP) from Sigma Aldrich and InvivoGen.

The differentiated THP-1 cells ($0.75 \times 10^6$ cells/ml) are placed in culture in 200 μl of complete medium, and then incubated in the presence of the various test samples.

Each analysis is carried out in triplicate.

The cell supernatants are collected in order to assay the secreted cytokines after 8 h of stimulation for TNF-α, and 20 h for RANTES.

The ELISA assays are carried out according to the indications given by the supplier.

Results

The first tests consisted in testing the synergistic potential of MDP and of f-MLP, and also the PGN/LPS combination, on the production of pro-inflammatory cytokines by the differentiated THP-1 cells.

The MDP was tested at the doses of 1, 10 and 100 μg/ml. The minimum dose does not induce a significant synergistic effect. On the other hand, the doses of 10 and 100 μg/ml have a similar synergistic activity on the production of RANTES and of TNF-α in response to the PGN and LPS.

Figure 2:
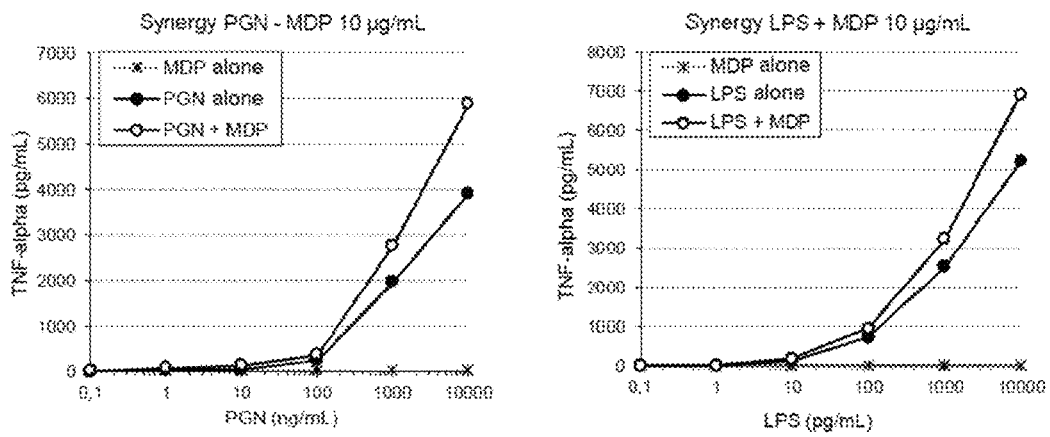
FIG. 2: Production of TNF-α in response to the PGN and to the LPS in THP-1 cells sensitized with MDP at 10 µg/ml.

The results presented in FIGS. 1 and 2 clearly show a synergistic effect of MDP on the production of RANTES. On the other hand, this synergistic effect is not very marked for TNF-α. Furthermore, the detection threshold (amount of PGN or of LPS giving a response greater than three times the SD of the background noise) is lower for RANTES (see Table 2).

Figure 3:
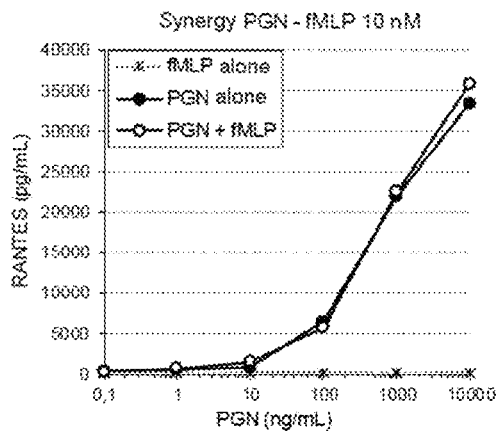
FIG. 3: Production of RANTES in response to the PGN in THP-1 cells sensitized with f-MLP (10 nM).

The f-MLP was used at the doses of 1 nM, 10 nM and 100 nM. However, no synergistic effect was observed in the THP-1 cells (FIG. 3).

Figure 4:
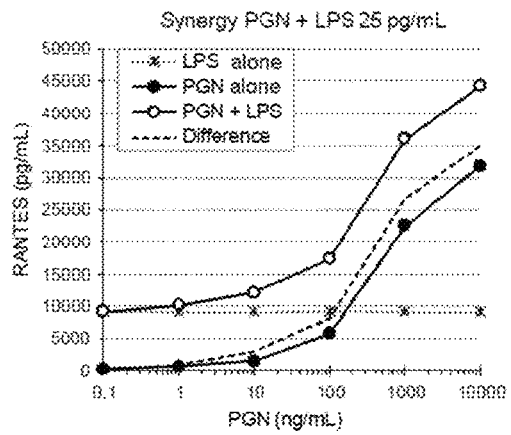
FIG. 4: Production of RANTES in response to the PGN in THP-1 cells sensitized with LPS (25 pg/ml).

The synergistic effect of the LPS was analyzed by adding a sub-optimal dose (25 pg/ml) to increasing doses of PGN (FIG. 4). The synergistic effect of the two agonists is visible after assaying the two cytokines. However, the LPS-induced synergistic effect on the production of RANTES remains less than that induced by MDP.

The response was quantified by measuring the production of RANTES and of TNF-α. In all cases, synergy is clearly visible for the RANTES assay, with a high sensitivity. This assay will therefore be preferred and retained for the rest of the experiments.

These results show that the addition of MDP at 10 μg/ml to THP-1 cells, with in return assaying of RANTES, is the most effective mode of sensitization for detecting low levels of PGN and of LPS. In theory, these detection thresholds should make it possible to detect the contaminants present in manufactured products.

These first analyses were carried out by diluting the standard inflammatory molecules in the presence of the I-10.01 polymer. The solutions were added to the THP-1 cells so as to obtain a final glucose polymer concentration of 5 mg/ml and a final cell density of $0.75 \times 10^6$ cells/ml. In order to increase the sensitivity of the assay, the tests were carried out while varying these two parameters.

Figure 5:
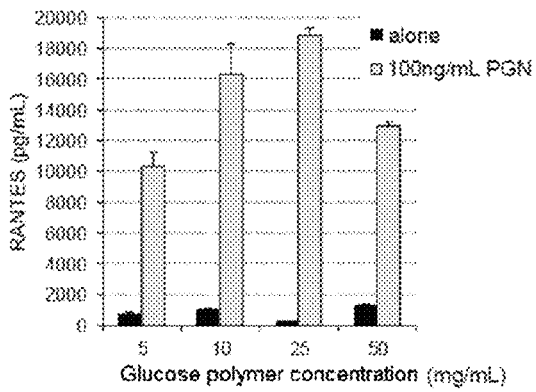
FIG. 5: Effect of the glucose polymer concentration on the production of RANTES induced by the PGN in the THP-1 cells.

The presence of the glucose polymer does not hamper the production of RANTES for concentrations less than or equal to 25 mg/ml. This increase in sensitivity is not linked to a pro-inflammatory effect of the polymer on the cells, since the response is identical to the background noise in the absence of PGN (FIG. 5).

Figure 6:
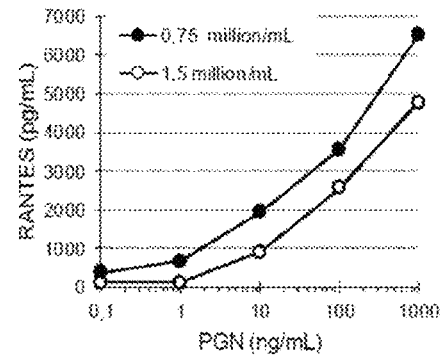
FIG. 6: Effect of the THP-1 cell concentration on the production of RANTES induced by the PGN.

On the other hand, increasing the cell density beyond $0.75 \times 10^6$/ml reduces the production of RANTES in response to PGN (exhaustion of the culture medium or cell modification) (FIG. 6).

The sensitivity tests with MDP at 10 μg/ml were reproduced three times for LPS and six times for PGN with THP-1 cells originating from distinct preparations. The data obtained made it possible to determine the detection thresholds and the EC50s (Table 2). For the estimation of the sensitivity, the values were brought to per g of polymer, with the concentration of 25 mg/ml being considered.

The synergistic effect induced by MDP is identical for LPS and PGN, since it makes it possible to increase the sensitivity of the THP-1 cells by a factor of 5 in both cases.

TABLE 2

Detection thresholds and EC50 for PGN and LPS in the sensitized THP-1 model.

| | PGN | PGN + MDP | LPS | LPS + MDP |
|---|---|---|---|---|
| Detection threshold | 14.5 ± 8.5 ng/ml | 2.8 ± 1.2 ng/ml | 10 ± 7 pg/ml | 2 ± 1 pg/ml |
| EC50 | 1.2 ± 0.7 μg/ml | 0.4 ± 0.2 μg/ml | 0.9 ± 0.1 ng/ml | 0.3 ± 0.1 ng/ml |
| Sensitivity | 580 ± 340 ng/g | 112 ± 48 ng/g | 400 ± 280 pg/g | 80 ± 40 pg/g |

These studies show that the sensitized THP-1 cells can be used to develop a sensitive inflammatory response test for detecting traces of contaminants in glucose polymer preparations.

The following experimental conditions are selected:
final concentration of differentiated THP-1 cells: $0.75 \times 10^6$ cells/ml,
sensitizing agent: MDP (S. aureus) at 10 µg/ml,
final glucose polymer concentration: 25 mg/ml,
response: ELISA assay of the production of RANTES after 20 h of stimulation.

In order to validate the method, the tests with the MDP-sensitized THP-1 cells were carried out with the samples presented in table 1.

Figure 7:
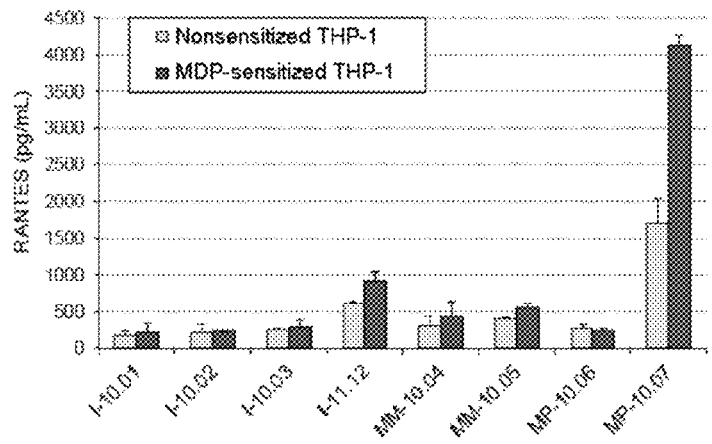
FIG. 7: Production of RANTES by the sensitized THP-1 cells in response to the various glucose polymer samples.

The test based on the production of RANTES by sensitized THP-1 cells makes it possible to detect the samples of polymers contaminated with LPS: polymers referenced I-11.12, MP-10.07 and, to a lesser extent, MM-10.04 and MM-10.05 (FIG. 7).

On the other hand, the samples contaminated only with PGN (e.g. I 10-02) do not give a response, thereby indicating that this cell test is more suitable for the detection of endotoxins. However, the amplitude of the responses is not directly proportional to the level of LPS measured using the LAL test (see, for example, the responses obtained with I-11.12 compared with MM-10.05), thereby suggesting that contaminants other than PGN probably act with LPS on the response of the THP-1 cells.

The THP-1 cells respond to the solutions of control PGN, but barely or not at all to the samples originating from batches contaminated only with natural PGN.

The size of the PGNs is very heterogeneous, and some of these molecules can reach impressive weights ($>10^6$ Da). The latter have low solubility, which affects their pro-inflammatory power but promotes their removal by filtration. On the other hand, the PGNs which are soluble, and consequently active, have an average weight of 120 kDa and are not removed by filtration. It is therefore possible to envision that the two Wako SLP tests enable an overall assaying of all the PGNs, whereas the cell test detects only the active PGNs.

EXAMPLE 3

Use of the HEK-BLUE (hTLR2, hNOD2, Null2) and RAW-BLUE (InvivoGen) Cell Lines for Detecting Contaminants Materials & Methods The HEK-BLUE cell lines (InvivoGen) are lines modified by stable transfection with vectors encoding innate immunity receptors. These cells are also cotransfected with a reporter gene which produces a secreted form of alkaline phosphatase (SEAP: secreted embryonic alkaline phosphatase), the synthesis of which is under the direct control of the signaling pathway associated with the receptor(s) expressed in the same cell line.

For the experiments relating to the detection of inflammatory contaminants, four lines are used:
HEK-BLUE hTLR2 line (HEK-TLR2): this line responds specifically to TLR2 agonists (in particular PGN and the majority of glycolipids and lipopeptides),
HEK-BLUE hNOD2 line (HEK-NOD2): this line responds to MDP and related molecules, such as monomeric PGNs,
HEK-BLUE Null2 line (HEK-Null): this is a control line, the use of which is necessary in order to verify that the glucose polymer solutions do not induce the production of the enzyme via an intrinsic mechanism,
RAW-BLUE line: this is a mouse macrophage line transfected with SEAP. This line, which naturally expresses virtually all the innate immunity receptors, is used as a positive control in the tests.

The RAW-BLUE and HEK-BLUE cells are cultured according to the supplier's recommendations. In particular, the selection pressure for the plasmids encoding the inflammatory molecule receptors (TLR2 or NOD2) and encoding the SEAP is provided by adding, to the culture medium, the HEK-BLUE Selection/blasticidin antibiotics. At 75% confluence, the cells are resuspended at a cell density of $0.28 \times 10^6$ cells/ml. Before stimulation, 180 µl of the cell suspension are distributed into the culture wells (96-well plate), i.e. 50 000 cells/well. The cells are then stimulated for 24 h by adding 20 µl of the test samples (in ten-times concentrated form). The stimulation lasts from 16 to 24 h.

The production of SEAP in response to the contaminated molecules is estimated by measuring the phosphatase activity according to the protocol supplied by the manufacturer: 20 µl of culture supernatant are diluted in 180 µl of QUANTI-BLUE. The color develops at 37° C. and the reading is carried out, at various times, at 620 nm. The data are expressed as absorbance after subtraction of the background noise, obtained by adding the same volume of nonconditioned culture medium to the reaction medium of the enzyme.

The optimization studies are carried out with I-10.01 glucose polymer solutions (table 1) artificially loaded with standard inflammatory molecules: PGN, LTA and MDP (source: S. aureus) and LPS (source: E. coli). The analyses are then carried out on the series of samples corresponding to various batches selected on the basis of the levels of contamination with PGN and LPS (Table 1).

Results

The HEK-BLUE cells are received in the form of frozen vials. Before beginning the inflammatory response tests, it is necessary to be sure of the resumption of growth of the cells and of their capacity to respond to inflammatory molecules. Furthermore, these transfected cells rapidly degenerate after several passages, which can result in a loss of the expression vectors for the innate immunity receptors, or even of the vector encoding the SEAP.

It is therefore recommended to verify the capacity of the cells to respond to inflammatory factors at the beginning of the placing in culture, and then after several subculturing steps. These tests are carried out with PGN for HEK-TLR2, MDP for HEK-NOD2 and TNF-α, the latter being a powerful activator of the NF-κB pathway. Indeed, HEK cells naturally possess the receptor of this cytokine, and will therefore produce SEAP (the expression vector of which is under the control of the NF-κB pathway) in response to TNF-α.

Figure 8:
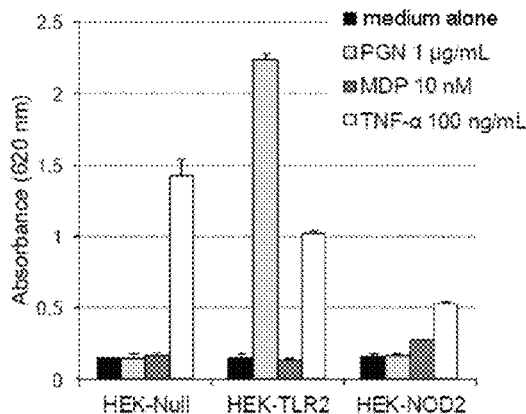
FIG. 8: HEK-BLUE cell response test. The cells were stimulated with PGN, MDP and TNF-α, which is a positive control for stimulation of the HEK-BLUE cells.

The results presented in FIG. 8 show the tests carried out in order to verify the resumption of growth of the three lines. As expected, the HEK-TLR2 and HEK-Null cells respond to TNF-α, with an equivalent production of SEAP. Furthermore, the HEK-Null line is insensitive to PGN and to MDP, whereas the HEK-TLR2 cell responds effectively only to PGN. These two lines have therefore acquired their phenotypic characteristics and it will be possible to use them for the rest of the experiments. In this example, the HEK-NOD2 line responds only very weakly to TNF-α and to MDP, thereby indicating that it has not acquired the expected characteristics.

Figure 9:
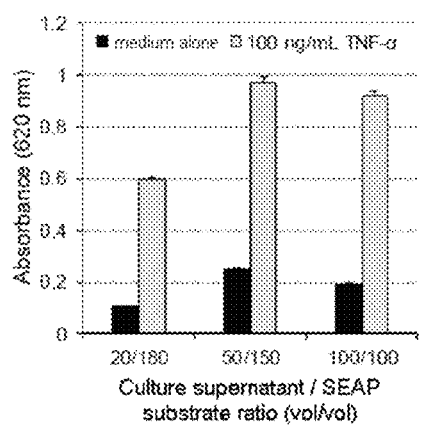
FIG. 9: SEAP response as a function of the volume of culture supernatant added to the reaction medium. The activation of the cells (HEK-TLR2) was carried out with TNF-α.

The response of the HEK-BLUE and RAW-BLUE cells to the pro-inflammatory molecules is directly linked to the production of SEAP. The supplier recommends adding 20 µl of culture supernatant to 180 µl of SEAP substrate. The experiments were therefore carried out under these conditions, and then optimized by increasing the volume of culture supernatant, and therefore the amount of enzyme in solution (FIG. 9).

The results show that the 50/150 ratio gives a higher response than the ratio recommended by the supplier. On the other hand, the ratio 100/100 is not more effective, probably due to a lack of SEAP substrate in the reaction medium.

Figure 10:
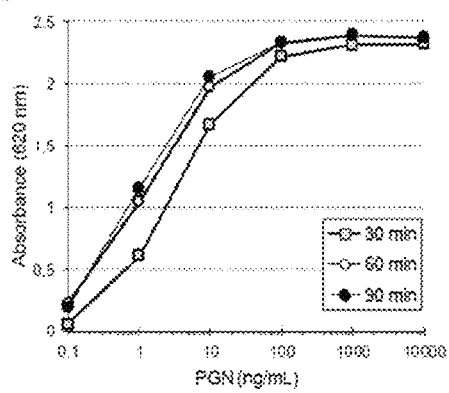
FIG. 10: Optimization of the reaction time between the SEAP and its substrate. The HEK-TLR2 (FIG. 10A) and RAW-BLUE (FIG. 10B) cells were stimulated in the presence of increasing concentrations of PGN. After 20 h of stimulation, the supernatants containing the SEAP were incubated in the presence of the QUANTI-BLUE solution at the times indicated, and then the absorbance was measured at 620 nm.
Figure 10:
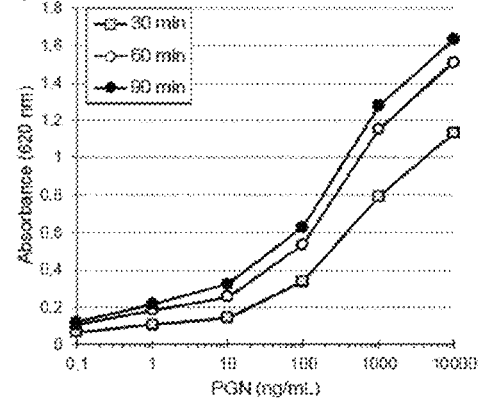

The intensity of the coloration (620 nm) is proportional to the amount of SEAP secreted by the cells, but also to the time for hydrolysis of the substrate by the enzyme. Various visualization times were therefore tested using the same supernatants of the PGN-activated HEK-TLR2 and RAW-BLUE cells (FIG. 10).

The optimum coloration is achieved starting from 60 min of reaction between the SEAP and its substrate for the HEK-TLR2 cells. A slight increase is also observed at 90 min for the RAW-BLUE cells, but this increase is probably linked to the fact that these cells produce less SEAP.

Figure 11:
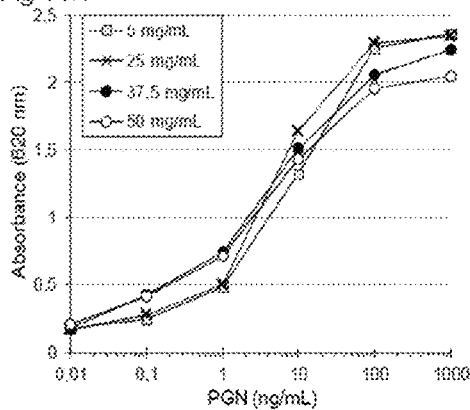
FIG. 11: Effect of the glucose polymer concentration on the production of SEAP by the HEK-TLR2 (FIG. 11A) and RAW-BLUE (FIG. 11B) cells in response to increasing concentrations of PGN.
Figure 11:
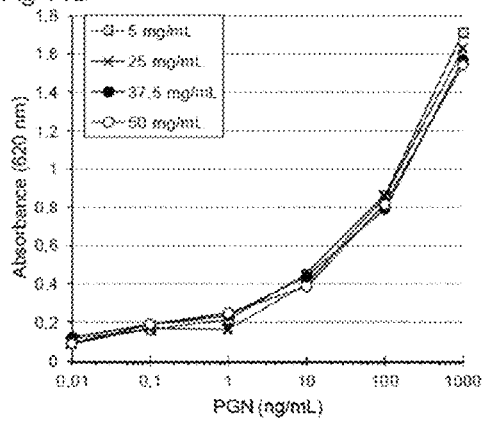

The effect of the glucose polymer concentration on the cell responses was analyzed by stimulating the HEK-TLR2 and RAW-BLUE cells with standard PGN diluted in medium supplemented with the I-10.01 polymer. The solutions were then added to the cells so as to obtain final polymer concentrations ranging from 5 to 50 mg/ml (FIG. 11).

The concentrations up to 37.5 mg/ml do not significantly modify the amplitude of the response to PGN in the HEK-TLR2 line. An improvement in the response to low concentrations of PGN is even noted for polymer concentrations above 25 mg/ml, probably linked to a better dispersion of the contaminant. As regards the RAW-BLUE cells, the production of SEAP is not modified, regardless of the glucose polymer concentration.

The HEK-NOD2 line shows a low amplitude of response to MDP and even to TNF-α, which appears to be linked to a high background noise. In these cells, the SEAP gene is under the control of a weak promoter, which is more sensitive to cell stress than that used for the other HEK-BLUE cells. In order to reduce the background noise and to increase the amplitude of the response to the contaminants, the culture conditions were modified so as to reduce the stress of the cells.

According to the supplier's recommendations, the cells at 75% confluence are resuspended at a density of $0.28 \times 10^6$ cells/ml, and then 180 µL of the cell suspension are distributed into the culture well (96-well plate), i.e. 50 000 cells/well, before stimulation in the course of the day.

Figure 12:
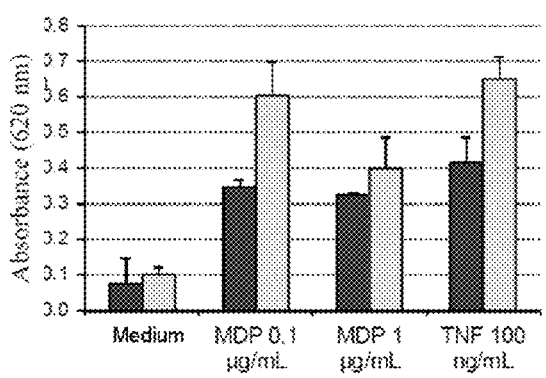
FIG. 12: Comparison of the SEAP responses of the HEK-NOD2 cells cultured according to the method provided by the supplier versus the improved procedure without a subculturing step before stimulation.
Figure 13:
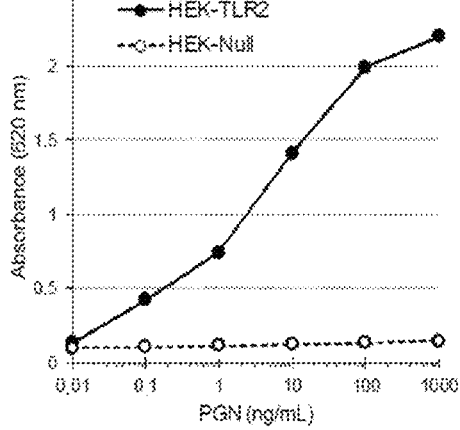
FIG. 13: Production of SEAP in response to the PGN in HEK-TLR2 and HEK-Null cells.
Figure 14:
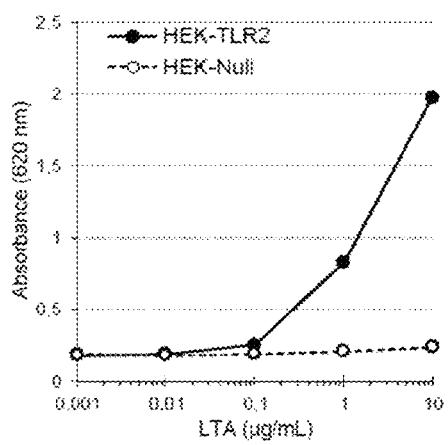
FIG. 14: Production of SEAP in response to the LTA in HEK-TLR2 and HEK-Null cells.

In the new procedure referred to as without subculturing, the HEK-NOD2 cells are conditioned in wells (10 000/well) and cultured for three days. Before stimulation, the culture medium is removed and replaced with a medium containing 1% of FCS and the solutions to be assayed. In this case, the SEAP response is 5-6 times greater than the negative control, which is compatible with a test for detecting MDP in contaminated solutions (FIG. 12).

These first studies show that the HEK-BLUE and RAW-BLUE cells can be used to develop sensitive inflammatory response tests for detecting traces of contaminants in glucose polymer preparations.

The following experimental conditions were selected:

final glucose polymer concentration: 37.5 mg/ml for the HEK-BLUE-cells, and 50 mg/ml for the RAW-BLUE cells, enzymatic reaction: 50 µl of conditioned medium+150 µl of SEAP reagent, minimum reaction time: 60 min.

FIGS. 13-16 show examples of assays of the SEAP activity produced by the HEK-TLR2 and RAW-BLUE cells in response to various inflammatory molecules.

The HEK-TLR2 cells respond very effectively to PUN, whereas the response to LTA is weaker. The responses are, however, more effective than those observed with cells of monocyte/macrophage type. In addition, the glucose polymer has no direct effect on the production of SEAP, since no response is observed in the supernatants of HEK-Null cells.

The RAW-BLUE cells respond well to PGN, but are less sensitive than the HEK-TLR2 cells. The response to LPS is weak and remains much lower than that observed when measuring the production of RANTES by the THP-1 cells.

Contrary to the other cell lines, the HEK-NOD2 cells respond effectively to MDP, which can be taken advantage of for detecting the PGN degradation products.

The experiments with the standard PGNs, LPS and MDP were reproduced with different cell preparations, which made it possible to determine the characteristics presented in table 3. For the estimation of the sensitivity, the values were brought to per g of polymer, with the concentration of 37.5 mg/ml being considered for the HEK-BLUE cells and 50 mg/ml for the RAW-BLUE cells.

TABLE 3

Detection thresholds and EC50 for PGN, LPS and MDP in the HEK-BLUE and RAW-BLUE models

| | HEK-TLR2 line | HEK-NOD2 line | RAW-BLUE line | |
| --- | --- | --- | --- | --- |
| | PGN | MDP | PGN | LPS |
| Detection threshold | 0.07 ± 0.04 ng/ml | 1.5 ± 0.5 ng/ml | 2.1 ± 1.5 ng/ml | 0.24 ± 0.06 ng/ml |
| EC50 | 3.1 ± 2.5 ng/ml | 12 ± 6 ng/ml | 210 ± 75 ng/ml | >10 ng/ml |
| Sensitivity | 1.9 ± 1.1 ng/g | 40 ± 13 ng/g | 42 ± 30 ng/g | 4.8 ± 1.2 ng/g |

The HEK-TLR2 and RAW-BLUE lines are very effective for detecting the PGNs at low concentrations. In particular, the HEK-TLR2 line detects PGN levels below 2 ng/g of glucose polymer, i.e. a sensitivity threshold which is 50 times greater than that obtained with the sensitized THP-1 cells. The RAW-BLUE line effectively detects small traces of PGN, but it is not very reactive with respect to LPS, with a detection threshold approximately 50 times greater than that of the sensitized THP-1 cells.

In order to validate these tests, the assays were therefore carried out with glucose polymer samples.

The HEK-TLR2 line makes it possible to detect contaminations in the I-10.02, I-11.12 and MM-10.05 batches, and, to a lesser extent, the MP-10.06 and MP-10.07 batches (the response observed with MM-10.04 is not significant in comparison with I-10.01 and is not therefore retained).

Figure 17:
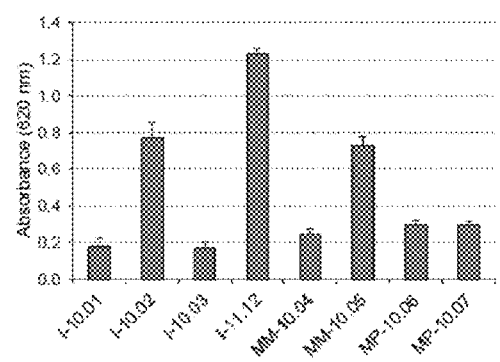
FIG. 17: SEAP activity in HEK-TLR2 cells in response to the various glucose polymer samples.

On the other hand, the I-10.03 sample is not detected, which can be correlated with the very low level of PGN, close to the limit of detection of the SLP-Wako test (FIG. 17).

While the positive responses obtained with I-10.02, I-11.12, MM-10.05 and MP-10.07 were expected, given the high level of PGN present in these four samples, it may be noted that there is no proportionality between the concentration given by the SLP test and the response of the cells.

Indeed, the I-10.02 and I-11.12 glucose polymers give the highest responses, whereas the PGN levels are less than 1 µg/g. Conversely, the MP-10.07 sample, which is the one with the highest PGN load, gives a response close to the background noise. PGNs are macromolecules of very variable weight, and it has been demonstrated that their reactivity is inversely proportional to their molecular weight. It can therefore be envisioned that the PGNs of I-10.02 and I-11.12 are smaller in size than the PGNs present in the MM-10.05 and MP-10.07 samples, which would explain their higher pro-inflammatory potential.

It is also surprising to see a response with the MP 10-06 batch, even though it does not contain PGN. However, the HEK-TLR2 cells react with other inflammatory molecules, such as lipopeptides, LTAs or LAMs (lipoarabinomannans), which are all TLR2 agonists. Thus, this result suggests that this sample which is uncontaminated in terms of absence of LPS and of PGN contains other pro-inflammatory molecules which are TLR2 agonists.

Figure 18:
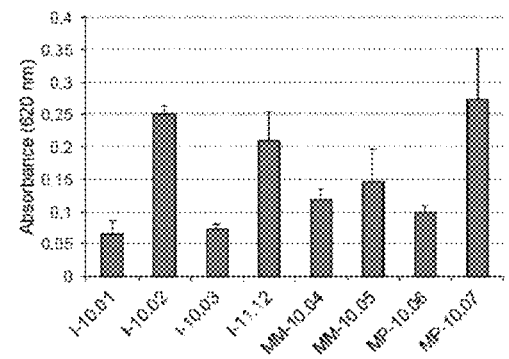
FIG. 18: SEAP activity in RAW-BLUE cells in response to the various glucose polymer samples.

With the exception of the I-10.01 and 1-10.03 samples, all the samples give a positive response with the RAW-BLUE cells (FIG. 18).

The level of LPS present in the I-10.02 sample is close to the detection threshold of the LAL test, which indicates that the response observed is due to the presence of PGN. This result confirms that, contrary to the THP-1 cells which do not respond to this sample, the RAW-BLUE cells are effective for detecting small contaminations with PGN. The strong response of the I-11.12, MM-10.05 and MP-10.07 batches therefore appears to be due to the presence of the two contaminants (PGN and LPS).

Like the HEK-TLR2 cells, the RAW-BLUE cells respond positively to MP-10.06, which confirms the presence of a contaminant other than LPS and PGNs in this sample.

Figure 19:
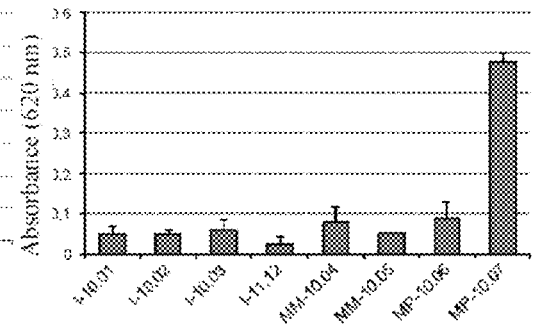
FIG. 19: SEAP activity in HEK-NOD2 cells in response to the various glucose polymer samples.

Finally, the HEK-NOD2 cells react strongly in the presence of MP-10.07, and give a weak but significant response with the I-10.03, MM-10.04 and MP-10.06 samples, which indicates that these samples were contaminated with PGNs during a step of their production, and that the latter were partially degraded during the course of production of the product (FIG. 19).

The HEK-TLR2 and RAW-BLUE cells are effective for detecting traces of inflammatory contaminants in products of I-10.01 and I-10.03 type.

They even have characteristics that are complementary to the sensitized THP-1 cells. Indeed, the tests using the three of them make it possible to detect the majority of inflammatory contaminants that may be present in glucose polymer samples.

THP-1: any inflammatory contaminant with a high reactivity for LPS.

RAW-BLUE: any inflammatory contaminant with a high reactivity for PGNs.

HEK-TLR2: specific for TLR2 agonists with a high reactivity for PGNs.

HEK-NOD2: specific for MDP and consequently for PGN degradation products. As for the THP-1 cells, an absence of proportionality between the levels of PGN and/or of LPS and the amplitudes of the cell responses is also noted.

This problem is doubtless linked to the size of these macromolecules and/or to their presence in the form of aggregates, which influences their reactivity with respect to the cells. Thus, it was observed that passing the standard PGN through a 0.22 µm filter reduces by approximately 50% the reactivity thereof for the HEK-TLR2 cells. Consequently, in all the tests, the glucose polymer solutions are prepared under aseptic conditions but without a step of filtration of the standard molecules.

EXAMPLE 4

Characterization of the Contaminants by Using the Sensitized THP-1, the HEK-BLUE (hTLR2, hNOD2) and the RAW-BLUE Cell Lines Examples 2 and 3 show that the sensitized THP-1, the HEK-TLR2, the HEK-NOD2 and the RAW-BLUE lines are effective for detecting traces of inflammatory contaminants in the glucose polymer samples. In addition to LPS and MDP, the presence of which is detected via the TLR4 and NOD2 receptors, the other contaminants that may be present in the samples are predominantly TLR2 ligands (PGN, LTA and lipopeptides). Consequently, the lines do not make it possible to establish the contribution of the PGNs in the TLR2-specific response. However, PGNs are macromolecules of which the weight ranges from ~100 kDa to several million Da. Conversely, LTAs and lipopeptides have low weights, less than 15 kDa. Thus, the introduction of an ultrafiltration step (30 kDa) should make it possible to retain the PGNs and to measure only the response to TLR2 ligands of small sizes.

Experimental Procedures

For the experiments relating to this example, the five cell lines presented in examples 2 and 3 are used:

THP-1 monocyte line: response to any inflammatory contaminant with a high reactivity for LPS, RAW-BLUE: line: response to any inflammatory contaminant with a high reactivity for PGNs, HEK-BLUE hTLR2 line: specific for TLR2 agonists with a high reactivity for PGNs, HEK-BLUE hNOD2 line: specific for PGN total depolymerization products (MDP), HEK-BLUE Null line: negative response control.

The glucose polymer samples are presented in example 2 (Table 1). These samples are prepared in solution at the concentrations described in examples 2 and 3. The cell responses (production of RANTES for the THP-1 cells and secretion of SEAP for the BLUE cells) are analyzed either with the nonfiltered samples: Total response, or with the filtrates obtained by ultrafiltration on a microconcentrator with a cut-off threshold at 30 kDa (Sartorius): Filtrate response.

Before use, the microconcentrators were treated with a saline solution (150 mM NaCl) prepared with non-pyrogenic water. The retentates and filtrates were tested with the cell lines, and only the filters giving a negative response in each test were retained for the analyses with the glucose polymer samples.

Results

Figure 20:
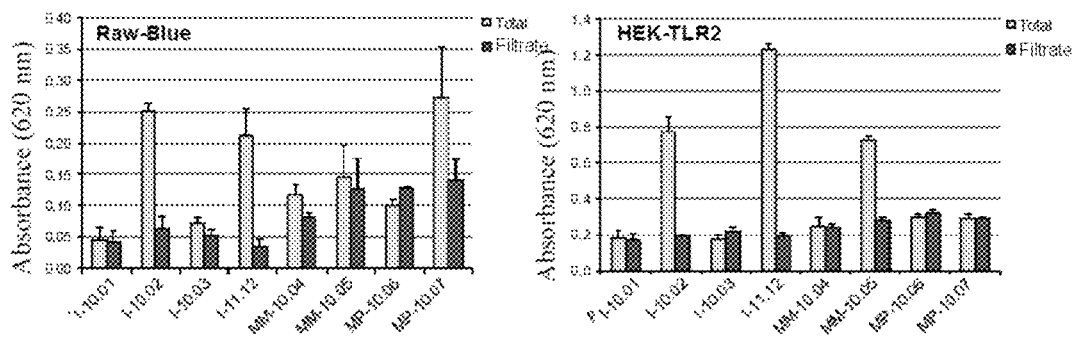
FIG. 20: SEAP production in RAW-BLUE and HEK-TLR2 cells in response to the various glucose polymer samples before (Total) and after ultrafiltration at 30 kDa (Filtrate).

The results presented in FIG. 20 show the responses of the HEK-TLR2 and RAW-BLUE cells obtained in the presence of the various samples before and after ultrafiltration.

The Total responses are similar to those observed in example 3 (FIGS. 17 and 18).

The Filtrate responses are greatly reduced for the I-10.02 and I-11.12 samples in the two cell types, with values close or equal to the detection thresholds. These data confirm that these two samples are contaminated with PGN, which was retained by the filter.

The filtrate response of MM-10.05 is reduced in the HEK-TLR2 cells, but not in the RAW-BLUE cells, indicating that this sample is contaminated with a combination of several molecules, with a considerable part contributed by PGN.

The MM-10.04, MP-10.06 and MP-10.07 samples are not significantly contaminated with PGN, since the Total and Filtrate responses are identical in the HEK-TLR2 cells. On the other hand, a 50% decrease in the Filtrate response can be noted for MP-10.07 in the RAW-BLUE cells. The LAL test showed that this sample is loaded with LPS. Although the weight of endotoxins is less than 30 kDa, these molecules are capable of forming aggregates, which may account for the loss of response after filtration.

The Total and Filtrate responses were analyzed in the THP-1, RAW-BLUE, HEK-TLR2 and HEK-NOD2 cell types. The results are given in Table 4.

For the HEK-NOD2 cells, the Total and Filtrate responses are identical, which was expected since MDP and the related molecules have a weight much less than 30 kDa (MW~500 Da). Only the Total responses are reproduced in Table 4.

MM-10.04: sample weakly contaminated with LPS and TLR2-activating molecules of small size (LTA, lipopeptides). The presence of MDP also points to PGN degradation products.

MM-10.05: sample contaminated with PGN and other molecules of small sizes. The weak responses of the other tests suggest the presence of traces of LPS and of other TLR2 ligands.

MP-10.06: sample contaminated with numerous small molecules. On the other hand, the weak THP-1 and HEK-TLR2 responses indicate the absence of PGN and of LPS.

MP-10.07: sample contaminated with numerous small molecules, with a high proportion of LPS and of MDP.

It may be noted that the results match the Wako SLP-HS assays for the I-10.01, I-10.02, I-10.03 and I-11.12 samples, which are final products, and the MM-10.04 and MP-10.06 samples, which were identified as being devoid of PGN.

On the other hand, the two MM-10.05 and MP-10.07 samples give PGN responses that are weaker than those expected with the data of the SLP tests. However, it is possible that these samples gave false positives with the SLP tests, via crossreaction with β-glucans, for example. Another possibility is that these samples contain very large PGNs, the low solubility of which prevents the triggering of a response in the cell tests.

EXAMPLE 5

Peptidoglycan Assay Method

The assay is based on the specific recognition of PGNs by a line expressing the TLR2 receptor and on the production

TABLE 4

Characterization of the contaminants by analysis of the cell responses.

| Response | I-10.01 | I-10.02 | I-10.03 | I-11.12 | MM-10.04 | MM-10.05 | MP-10.06 | MP-10.07 |
|---|---|---|---|---|---|---|---|---|
| THP-1 | − | − | ± | + | + | ± | ± | + |
| <30 kDa | − | − | ± | ± | ± | ± | ± | ± |
| RAW-BLUE | − | + | ± | + | ± | + | ± | + |
| <30 kDa | − | − | − | − | ± | ± | ± | + |
| HEK-TLR2 | − | ++ | ± | +++ | ± | ++ | ± | ± |
| <30 kDa | − | − | ± | − | ± | ± | ± | ± |
| HEK-NOD2 | − | − | ± | − | + | − | + | ++ |
| Major effect | negative | PGN | residues | PGN | residues including MDP | PGN and residues | residues including MDP | LPS and residues |

The contamination levels are expressed as a function of the threshold limits of detection (LOD) and of the EC50s defined in examples 2 and 3 for each cell type (Tables 2 and 3), with the dose-response curves with respect to LPS for the sensitized THP-1 cells, with respect to PGN for the RAW-BLUE and HEK-TLR2 lines, and with respect to MDP for the HEK-NOD2 line: (−): level < LOD; (±): LOD ≤ level < 3 × LOD; (+): 3 × LOD ≤ level < 0.3 × EC50; (++): 0.3 × EC50 ≤ level < 3 × EC50; (+++): level ≥ 3 × EC50

The data make it possible to characterize the types of contaminants present in each glucose polymer solution and to establish their contribution in the inflammatory response:

I-10.01: sample not contaminated.

I-10.02: sample strongly contaminated with PGN. The absence of response of the THP-1 and HEK-NOD2 cells and of the Filtrates indicates that the contribution of the other contaminants is negligible.

I-10.03: sample weakly contaminated with residues probably originating from degradation products of small size. Indeed, the Total and Filtrate responses are at the limit of the background noise in all the tests.

I-11.12: sample strongly contaminated with PGN. The weak response of the THP-1 cells also points to traces of LPS.

of an enzymatic activity that is measurable via the activation of the signaling pathway associated with TLR2.

Experimental Procedures

For the experiments relating to this assay, two lines are used:

HEK-BLUE hTLR2 line;

HEK-BLUE Null2 line.

The two lines are presented in example 3.

Establishment of the Dose-Response Curve

Figure 21:
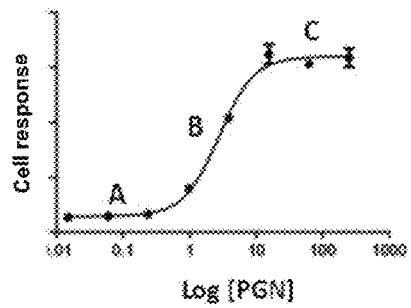
FIG. 21: Calibration curve of the cell response as a function of the level of S. aureus PGN.
Figure 21:
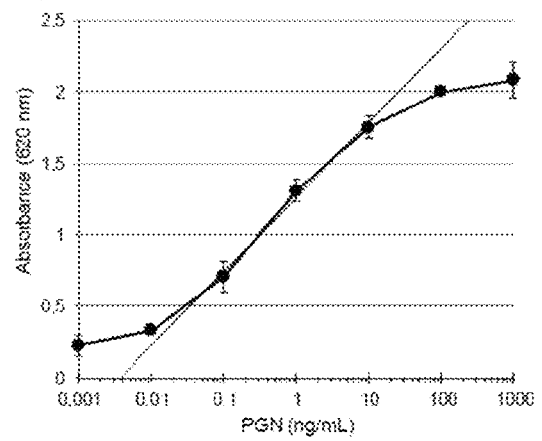

The dose-response curve was produced with standard *S. aureus* PGN (FIG. 21).

The HEK-BLUE cells are incubated with increasing concentrations of standard, and the cell response is measured by quantifying the enzymatic activity produced.

The result is a conventional sigmoid cell response curve:

part (A) corresponds to the responses obtained with low concentrations of PGN, below those which give effective activation of TLR2. This nonlinear zone therefore corresponds to the threshold limit of detection of the method. In such a way as to include the variability of the method, this detection threshold is estimated at three times the value of the background noise (response obtained in the absence of stimulus).

part (B) is the most interesting since a linear response is observed. This effective-response zone makes it possible to determine a direct relationship between the cell response and the level of PGN. It is therefore the assaying zone;

part (C) corresponds to a saturation of the cell response in the presence of PGN concentrations which are too high. There is in fact a saturation of the TLR2 receptors.

The standard curve for response of the HEK-TLR2 cells to PGN exhibits a linearity zone for concentrations between 0.07 and 10 ng/ml (i.e. between 2 and 267 ng/g).

In the case of samples that may be highly contaminated with PGN, it will be necessary to perform several serial dilutions so as always to be in the linearity zone. Conversely, low PGN concentrations require a step of concentrating the sample if it is desired to increase the sensitivity of the assay.

Sample Preparation

The PGN assays are carried out on glucose polymer solutions. The sample requiring the PGN quantification is incubated with HEK-BLUE hTLR2 cells, and the cell response is measured by quantifying the enzymatic activity produced. The amount of PGN contained in the sample can be determined by referring to the dose-response curves.

Figure 15:
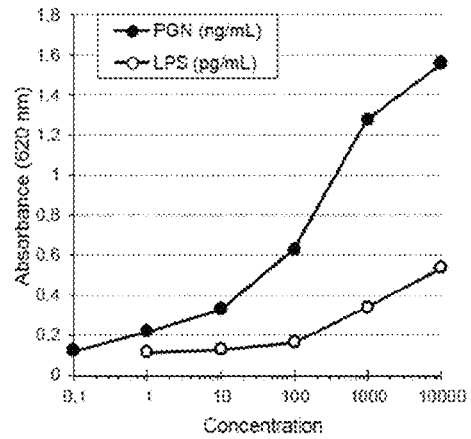
FIG. 15: Production of SEAP in response to the PGN and to the LPS in RAW-BLUE cells.
Figure 16:
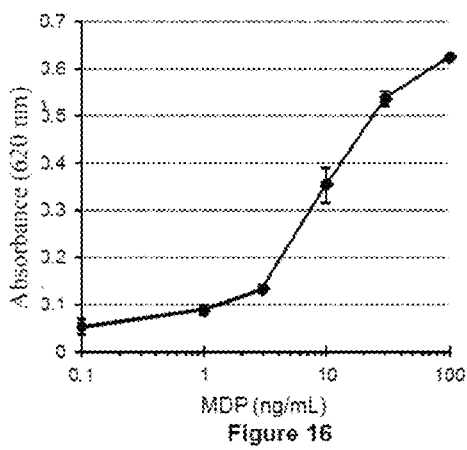
FIG. 16: Production of SEAP in response to the MDP in HEK-NOD2 cells.

The first tests were carried out with contaminated samples originating from manufactured glucose polymer batches (example 3, FIG. 15).

The HEK-TLR2 cells make it possible to detect the presence of PGN in the majority of the samples. On the other hand, it was observed that there is no correlation between the PGN levels measured by the SLP-Wako method and the amplitudes of the cell responses to PGN. Indeed, the samples with the highest PGN load are not those which induce the strongest production of SEAP.

By way of illustration, the MP-10.07 sample, which is the one most highly loaded with PGN (645 ng/mg), does not give a marked cell response with the HEK-TLR2 cells. Conversely, the I-10.02 and I-11.12 samples are less contaminated (253 and 393 ng/g, respectively), but are the most reactive in terms of cell response.

PGNs have very heterogeneous sizes. The heaviest forms (>$10^6$ Da) have low solubility and are therefore not very reactive in the cell tests. On the other hand, they are assayed by the SLP-Wako test. The PGNs of intermediate size (~100 kDa) are very soluble and are powerful inducers of TLR2. Despite low levels, they are capable of triggering a strong inflammatory response. This size dispersion and therefore activity dispersion is a major drawback for relating the contamination level to the risk of developing an inflammatory response when conventional quantitative assays are used (LAL and SLP-Wako).

The PGNs present in the I-10.02 and I-11.12 samples are soluble and therefore very reactive. Conversely, the MP-10.07 sample probably contains PGNs of large size, which will be removed in the course of the production of the final product.

On the basis of these first results, the PGN assay method based on the use of the HEK-TLR2 cells would therefore make it possible to quantify the biologically active PGNs capable of causing inflammatory reactions in vivo.

A particularly advantageous procedure for assaying the PGNs capable of triggering an inflammatory response is to reduce their size, and therefore increase their solubility for the in vitro cell response test.

Mutanolysin is an enzyme which, through its muramidase activity, is capable of depolymerizing PGNs. In order to test its activity, solutions of standard (*S. aureus*) PGN were prepared by diluting the molecule in culture medium in the absence or in the presence of the I-10.01 polymer (noncontaminated polymer) at the concentrations of 7.5% and 37.5% (weight/volume).

The samples were treated in the presence of 2500 U/ml of mutanolysin for 16 h at 37° C., and then added to the HEK-TLR2 cells. The cell response was measured by following the activity of the SEAP produced, according to the conditions described in example 3.

In the absence of glucose polymer, the treatment with mutanolysin for 16 h reduces the response of the HEK-TLR2 cells by more than 50%, indicating that the depolymerization was too strong and reduced the reactivity of the PGN with respect to the cells. Conversely, the presence of the glucose polymer reduces the activity of the enzyme, since the response of the cells is even improved in the presence of 7.5% of polymer, whereas it is unchanged in the presence of 37.5% of polymer.

Mutanolysin alone does not induce any cell response, indicating that it is not contaminated and that it has no activating effect on the cells.

In order to verify the effect of this treatment, the I-10.01, I-10.02, I-10.03, I-11.12, MM-10.05 and MP-10.07 polymers were diluted to the concentration of 7.5% and then treated for 16 h at 37° C. in the absence or in the presence of 2500 U/ml of mutanolysin.

The cell response was induced by adding 40 µl to 160 µl of cell suspension (final polymer concentration: 15 mg/ml).

Results

The responses of the HEK-TLR2 cells in the presence of the untreated polymers are weak, which was expected given the lower polymer concentration compared with example 3.

Figure 22:
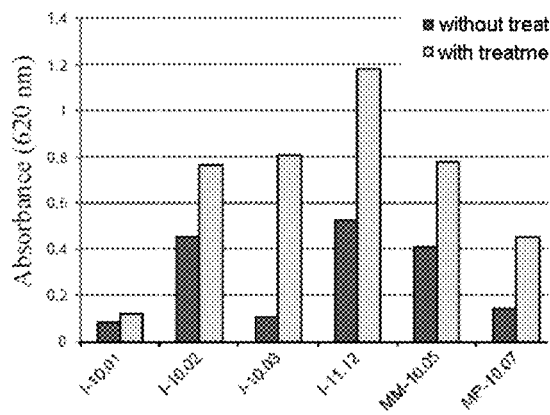
FIG. 22: SEAP activity in HEK-TLR2 cells in response to various glucose polymer samples before and after treatment with the mutanolysin.

After mutanolysin treatment, the responses to the glucose polymer solutions are clearly increased (FIG. 22). In addition, it may be noted that the I-10.03 polymer gives a response equivalent to the I-10.02 and MM-10.05 polymers, even though it was not reactive in the previous tests.

These results indicate that the mutanolysin partially depolymerized and therefore solubilized PGNs which were totally or partially insoluble owing to their excessively large size.

Figure 23:
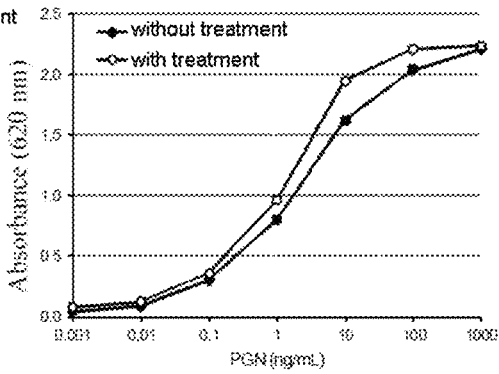
FIG. 23: SEAP production by HEK-TLR2 cells in response to the PGN before and after treatment with the mutanolysin.

The absorbance values were reported on the calibration curves established under the same conditions with the standard PGN (FIG. 23), so as to determine the PGN concentrations present in the glucose polymers.

The results expressed as ng of PGN/g of glucose polymer are reported in table 5. After mutanolysin treatment, the values are lower than those obtained with the SLP-Wako tests, but they reflect the load of the glucose polymers in terms of PGN with pro-inflammatory activity (Table 1).

The I-10.03 polymer gives a high value, close to I-10.02, after mutanolysin treatment. This piece of data is interesting since the two polymers have been the subject of complaint owing to episodes of aseptic peritonitis. The mutanolysin treatment of I-10.03 therefore made it possible to reveal the active PGN load, probably by enabling the contaminant to be solubilized.

The values of the MM-10.05 and MP-10.07 samples remain lower than those obtained with the SLP tests. However, these samples are contaminated with other inflammatory molecules other than PGNs. These molecules, and in particular the β-glucans, probably interfered in the SLP assays, increasing the response of the SLP tests.

TABLE 5

Assaying of PGNs present in the glucose polymers before and after mutanolysin treatment. The values are expressed in ng S. aureus PGN equivalent/g of polymer.

|  | I-10.01 | I-10.02 | I-10.03 | I-11.12 | MM-10.05 | MP-10.07 |
| --- | --- | --- | --- | --- | --- | --- |
| without treatment | <2 | 13.5 | <2 | 17.5 | 11.5 | 3.5 |
| with treatment | <2 | 33.5 | 36.8 | 113.5 | 36 | 13.5 |

The invention claimed is:

1. A method for detecting pro-inflammatory contaminants in a composition comprising glucose polymers, the method comprising:
   contacting a plurality of cell lines with the composition comprising glucose polymers, each of the plurality of cell lines expressing one or more Toll-Like Receptors (TLRs) or Nucleotide-binding Oligomerization Domain-containing protein-like receptors (NOD), wherein the plurality of cell lines comprises:
   a) a cell line expressing TLR2 and containing a reporter gene encoding a secreted form of alkaline phosphatase under the direct control of the TLR2 signaling pathway;
   b) a cell line expressing NOD2 and containing a reporter gene encoding a secreted form of alkaline phosphatase under the direct control of the NOD2 signaling pathway;
   c) a cell line expressing TLR4 and containing a reporter gene encoding a secreted form of alkaline phosphatase under the direct control of the TLR4 signaling pathway;
   d) a cell line expressing TLR2, TLR4 and NOD2 and containing a reporter gene encoding a secreted form of alkaline phosphatase under the direct control of the TLR2, TLR4 or NOD2 signaling pathway; and
   e) a negative control cell line;
   measuring activity of the secreted form of alkaline phosphatase; and identifying, based on the higher alkaline phosphatase activity in any of the cell lines a) to d) compared to the negative control, the presence, in the composition, of proinflammatory contaminants capable of activating one or more innate immunity receptors and triggering an inflammatory reaction.

2. The method of claim 1, wherein the composition comprising glucose polymers is for peritoneal dialysis, for enteral feeding, for parenteral feeding or for feeding newborn babies.

3. The method of claim 1, wherein the method further comprises:
   contacting a macrophage cell line with the composition of glucose polymers that may contain pro-inflammatory contaminants;
   measuring the production of Chemokine (C-C motif) ligand 5 (RANTES) by the macrophage cell line; and
   identifying, based on the production of RANTES, the presence, in the composition comprising glucose polymers, of contaminants capable of triggering an inflammatory reaction.

4. The method of claim 3, wherein a molecule chosen from muramyl dipeptide (MDP), L18-MDP, glycolyl-MDP, formyl-Met-Leu-Phe or lipopolysaccharide (LPS) is added to the composition comprising glucose polymers.

5. The method of claim 4, wherein MDP or LPS is added to the composition comprising glucose polymers.

6. The method of claim 3, wherein the production of RANTES is measured under one or more of the following conditions:
   the macrophage cell line is used at a density of between $0.5 \times 10^6$ and $1 \times 10^6$ cells/ml; and/or
   the glucose polymer concentration in the culture medium is less than 50 mg/ml; and/or
   the RANTES production is measured after 20 h of contacting; and/or
   MDP is added to the composition comprising glucose polymers at a concentration of between 1 and 100 µg/ml.

7. The method of claim 3, said method comprising detecting glucose polymer contamination with peptidoglycans (PGNs) and/or LPS.

8. The method of claim 1, wherein said method detects contamination with MDPs, wherein the detection of MDPs is performed with the cell line expressing NOD2 and containing a reporter gene encoding an alkaline phosphatase under the direct control of the NOD2 signaling pathway.

9. The method of claim 1, wherein said method detects contamination with PGNs, wherein the detection of PGNs is performed with the cell line expressing TLR2 and containing a reporter gene encoding an alkaline phosphatase under the direct control of the TLR2 signaling pathway.

10. The method of claim 1, wherein the composition comprising glucose polymers has a polymer concentration from 5 to 50 mg/ml.

11. The method of claim 1, wherein said method comprises:
    a step of treating the composition comprising glucose polymers with a mutanolysin prior to said contacting with the plurality of cell lines; or
    a step of filtering the composition comprising glucose polymers with a cut-off threshold of between 30 kD and 150 kD and contacting the filtrate with the plurality of cell lines, and optionally, comparing the results of the filtrate polymers contacted with the plurality of cell lines with the results of an unfiltered composition comprising glucose polymers contacted with the plurality of cell lines.

12. The method of claim 1, wherein said method also comprises a step of identifying or quantifying the contaminant(s) capable of triggering an inflammatory reaction.

13. The method of claim 1, wherein the method comprises quantifying the proinflammatory contaminant, wherein the contaminant is peptidoglycans (PGNs), and wherein the quantification of PGNs is performed with the cell line expressing TLR2 and containing the reporter gene encoding the secreted form of alkaline phosphatase under the direct control of TLR2 signaling pathway.

14. The method of claim 13, wherein said method comprises a step of treating the composition comprising glucose polymers with a mutanolysin, a step of incubating mutanolysin treated and untreated glucose polymer compositions with said plurality of cell lines, and a step of quantifying the PGNs.

15. The method of claim 1, wherein said plurality of cell lines comprise:
  a) an HEK293 cell line that stably co-expresses the human TLR2 and NF-κB-inducible secreted embryonic alkaline phosphatase (SEAP);
  b) an HEK293 cell line that stably co-expresses the human NOD2 and NE-KB-inducible SEAP;
  c) an HEK293 cell line that stably co-expresses the human TLR4 and NF-κB-inducible SEAP;
  d) a RAW 264.7 cell line that stably express SEAP gene inducible by NF-κB and activator protein 1 (AP-1) transcription factor; and
  e) an HEK293 cell line expressing SEAP gene under the control of the interleukin-12 (IL-12) p40 minimal promoter fused to five NF-κB and AP-1 binding sites.

16. The method of claim 3, wherein said macrophage cell line is THP-1.

* * * * *

UNITED STATES PATENT AND TRADEMARK OFFICE
CERTIFICATE OF CORRECTION

PATENT NO. : 9,494,576 B2  
APPLICATION NO. : 14/110569  
DATED : November 15, 2016  
INVENTOR(S) : Pierre Lanos et al.

Page 1 of 1

It is certified that error appears in the above-identified patent and that said Letters Patent is hereby corrected as shown below:

In the Specification

Column 13,
Line 31, "β-glucans. MDP" should read --β-glucans, MDP--.

Column 18,
Line 21, "(5 to 101)" should read --(5 to 10 I)--.

Column 24,
Line 23, "PUN," should read --PGN,--.

In the Claims

Column 33,
Line 7, "NE-KB-inducible" should read --NF-κB-inducible--.

Signed and Sealed this  
Fourth Day of April, 2017

Michelle K. Lee  
*Director of the United States Patent and Trademark Office*